(12) United States Patent
Hafezi et al.

(10) Patent No.: US 8,784,308 B2
(45) Date of Patent: Jul. 22, 2014

(54) INTEGRATED INGESTIBLE EVENT MARKER SYSTEM WITH PHARMACEUTICAL PRODUCT

(75) Inventors: Hooman Hafezi, Redwood City, CA (US); Robert Duck, San Francisco, CA (US); Timothy Robertson, Belmont, CA (US); Benedict Costello, Berkeley, CA (US)

(73) Assignee: Proteus Digital Health, Inc., Redwood City, CA (US)

( * ) Notice: Subject to any disclaimer, the term of this patent is extended or adjusted under 35 U.S.C. 154(b) by 0 days.

(21) Appl. No.: 13/319,309

(22) PCT Filed: Dec. 2, 2010

(86) PCT No.: PCT/US2010/058721
§ 371 (c)(1),
(2), (4) Date: Nov. 7, 2011

(87) PCT Pub. No.: WO2011/068963
PCT Pub. Date: Jun. 9, 2011

(65) Prior Publication Data
US 2012/0116359 A1    May 10, 2012

Related U.S. Application Data

(60) Provisional application No. 61/266,103, filed on Dec. 2, 2009.

(51) Int. Cl.
*A61B 5/00* (2006.01)
*A61K 9/48* (2006.01)
*A61B 5/06* (2006.01)
*A61B 5/07* (2006.01)
*A61J 3/00* (2006.01)
*A61K 9/00* (2006.01)

(52) U.S. Cl.
CPC ............ *A61K 9/0097* (2013.01); *A61K 9/4825* (2013.01); *A61K 9/4833* (2013.01); *A61J 3/007* (2013.01); *A61B 5/06* (2013.01); *A61B 5/073* (2013.01); *A61B 5/42* (2013.01); *A61B 5/4833* (2013.01); *A61B 5/4839* (2013.01); *A61B 5/6861* (2013.01); *A61B 5/6871* (2013.01); *A61B 5/6873* (2013.01); *A61J 2205/60* (2013.01); *A61J 2200/30* (2013.01); *Y10S 128/903* (2013.01)
USPC ............ 600/300; 424/9.1; 424/400; 424/408; 424/438; 424/439; 600/301; 600/372; 600/373; 604/890.1; 604/891.1; 604/892.1; 340/540; 128/903; 205/57; 156/60; 156/349

(58) Field of Classification Search
CPC ............ A61B 5/06; A61B 5/073; A61B 5/42; A61B 5/4833; A61B 5/4839; A61B 5/6861; A61B 5/6871; A61B 5/6873; A61K 9/0097; A61K 9/4825; A61K 9/4833; A61J 2205/60; A61J 2205/30
USPC .......... 424/9.1, 400, 408, 438, 439–441, 464, 424/474, 489–490, 43; 600/300–301, 372, 600/373; 604/890.1, 891.1, 891.2; 340/540, 340/573.1, 870.01; 205/57–66; 156/60, 349
See application file for complete search history.

(56) References Cited

U.S. PATENT DOCUMENTS

| | | |
|---|---|---|
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,752 A | 12/1977 | Butler |
| 4,077,397 A | 3/1978 | Ellis |

| | | | | | | |
|---|---|---|---|---|---|---|
| 4,077,398 A | 3/1978 | Ellis | | 6,122,351 A | 9/2000 | Schlueter, Jr. et al. |
| 4,082,087 A | 4/1978 | Howson | | 6,141,592 A | 10/2000 | Pauly |
| 4,090,752 A | 5/1978 | Long | | 6,200,265 B1 | 3/2001 | Walsh et al. |
| 4,106,348 A | 8/1978 | Auphan | | 6,206,702 B1 | 3/2001 | Hayden et al. |
| 4,129,125 A | 12/1978 | Lester | | 6,217,744 B1 | 4/2001 | Crosby |
| 4,166,453 A | 9/1979 | McClelland | | 6,231,593 B1 | 5/2001 | Meserol |
| 4,239,046 A | 12/1980 | Ong | | 6,245,057 B1 | 6/2001 | Sieben et al. |
| 4,251,795 A | 2/1981 | Shibasaki et al. | | 6,269,058 B1 | 7/2001 | Yamanoi et al. |
| 4,269,189 A | 5/1981 | Abraham | | 6,285,897 B1 | 9/2001 | Kilcoyne et al. |
| 4,331,654 A | 5/1982 | Morris | | 6,287,252 B1 | 9/2001 | Lugo |
| 4,345,588 A | 8/1982 | Widder et al. | | 6,288,629 B1 | 9/2001 | Cofino et al. |
| 4,418,697 A | 12/1983 | Tama | | 6,289,238 B1 | 9/2001 | Besson et al. |
| 4,425,117 A | 1/1984 | Hugemann | | 6,315,719 B1 | 11/2001 | Rode et al. |
| 4,439,196 A | 3/1984 | Higuchi | | 6,342,774 B1 | 1/2002 | Kreisinger et al. |
| 4,494,950 A | 1/1985 | Fischell | | 6,358,202 B1 | 3/2002 | Arent |
| 4,559,950 A | 12/1985 | Vaughan | | 6,364,834 B1 | 4/2002 | Reuss |
| 4,564,363 A | 1/1986 | Bagnall et al. | | 6,366,206 B1 | 4/2002 | Ishikawa et al. |
| 4,635,641 A | 1/1987 | Hoffman | | 6,371,927 B1 | 4/2002 | Brune |
| 4,654,165 A | 3/1987 | Eisenberg | | 6,374,670 B1 | 4/2002 | Spelman |
| 4,663,250 A | 5/1987 | Ong et al. | | 6,380,858 B1 | 4/2002 | Yarin et al. |
| 4,669,479 A | 6/1987 | Dunseath | | 6,394,997 B1 | 5/2002 | Lemelson |
| 4,687,660 A | 8/1987 | Baker et al. | | 6,426,863 B1 | 7/2002 | Munshi |
| 4,725,997 A | 2/1988 | Urquhart et al. | | 6,432,292 B1 | 8/2002 | Pinto et al. |
| 4,763,659 A | 8/1988 | Dunseath | | 6,440,069 B1 | 8/2002 | Raymond et al. |
| 4,767,627 A | 8/1988 | Caldwell et al. | | 6,441,747 B1 | 8/2002 | Khair |
| 4,784,162 A | 11/1988 | Ricks | | 6,453,199 B1 | 9/2002 | Kobozev |
| 4,793,825 A | 12/1988 | Benjamin et al. | | 6,477,424 B1 | 11/2002 | Thompson et al. |
| 4,844,076 A | 7/1989 | Lesho | | 6,496,705 B1 | 12/2002 | Ng et al. |
| 4,876,093 A | 10/1989 | Theeuwes et al. | | 6,526,315 B1 | 2/2003 | Inagawa |
| 4,896,261 A | 1/1990 | Nolan | | 6,531,026 B1 | 3/2003 | Takeichi et al. |
| 4,975,230 A | 12/1990 | Pinkhasov | | 6,544,174 B2 | 4/2003 | West |
| 4,987,897 A | 1/1991 | Funke | | 6,564,079 B1 | 5/2003 | Cory |
| 5,016,634 A | 5/1991 | Vock et al. | | 6,572,636 B1 | 6/2003 | Hagen et al. |
| 5,079,006 A | 1/1992 | Urquhart | | 6,577,893 B1 | 6/2003 | Besson et al. |
| 5,167,626 A | 12/1992 | Casper | | 6,579,231 B1 | 6/2003 | Phipps |
| 5,176,626 A | 1/1993 | Soehendra | | 6,595,929 B2 | 7/2003 | Stivoric |
| 5,261,402 A | 11/1993 | DiSabito | | 6,605,038 B1 | 8/2003 | Teller |
| 5,263,481 A | 11/1993 | Axelgaard et al. | | 6,609,018 B2 | 8/2003 | Cory |
| 5,279,607 A | 1/1994 | Schentag et al. | | 6,612,984 B1 | 9/2003 | Kerr |
| 5,281,287 A | 1/1994 | Lloyd | | 6,632,175 B1 | 10/2003 | Marshall |
| 5,283,136 A | 2/1994 | Peled et al. | | 6,632,216 B2 | 10/2003 | Houzego et al. |
| 5,305,745 A | 4/1994 | Zacouto | | 6,635,279 B2 | 10/2003 | Kolter et al. |
| 5,318,557 A | 6/1994 | Gross | | 6,643,541 B2 | 11/2003 | Mok et al. |
| 5,394,882 A | 3/1995 | Mawhinney | | 6,654,638 B1 | 11/2003 | Sweeney |
| 5,395,366 A | 3/1995 | D'Andrea et al. | | 6,663,846 B1 | 12/2003 | McCombs |
| 5,436,091 A | 7/1995 | Shackle et al. | | 6,673,474 B2 | 1/2004 | Yamamoto |
| 5,443,461 A | 8/1995 | Atkinson et al. | | 6,680,923 B1 | 1/2004 | Leon |
| 5,443,843 A | 8/1995 | Curatolo et al. | | 6,689,117 B2 | 2/2004 | Sweeney et al. |
| 5,458,141 A | 10/1995 | Neil et al. | | 6,694,161 B2 | 2/2004 | Mehrotra |
| 5,485,841 A | 1/1996 | Watkin et al. | | 6,704,602 B2 | 3/2004 | Berg et al. |
| 5,567,210 A | 10/1996 | Bates et al. | | 6,720,923 B1 | 4/2004 | Hayward et al. |
| 5,596,302 A | 1/1997 | Mastrocola et al. | | 6,738,671 B2 | 5/2004 | Christophersom et al. |
| 5,600,548 A | 2/1997 | Nguyen et al. | | 6,740,033 B1 | 5/2004 | Olejniczak et al. |
| 5,634,468 A | 6/1997 | Platt | | 6,745,082 B2 | 6/2004 | Axelgaard et al. |
| 5,645,063 A | 7/1997 | Straka et al. | | 6,755,783 B2 | 6/2004 | Cosentino |
| 5,705,189 A | 1/1998 | Lehmann et al. | | 6,757,523 B2 | 6/2004 | Fry |
| 5,738,708 A | 4/1998 | Peachey et al. | | 6,759,968 B2 | 7/2004 | Zierolf |
| 5,740,811 A | 4/1998 | Hedberg | | 6,773,429 B2 | 8/2004 | Sheppard et al. |
| 5,757,326 A | 5/1998 | Koyama et al. | | 6,800,060 B2 | 10/2004 | Marshall |
| 5,792,048 A | 8/1998 | Schaefer | | 6,801,137 B2 | 10/2004 | Eggers et al. |
| 5,802,467 A | 9/1998 | Salazar | | 6,822,554 B2 | 11/2004 | Vrijens et al. |
| 5,833,716 A | 11/1998 | Bar-Or | | 6,836,862 B2 | 12/2004 | Erekson et al. |
| 5,845,265 A | 12/1998 | Woolston | | 6,839,659 B2 | 1/2005 | Tarassenko et al. |
| 5,862,803 A | 1/1999 | Besson | | 6,840,904 B2 | 1/2005 | Goldberg |
| 5,868,136 A | 2/1999 | Fox | | 6,842,636 B2 | 1/2005 | Perrault |
| 5,925,030 A | 7/1999 | Gross et al. | | 6,845,272 B1 | 1/2005 | Thomsen |
| 5,957,854 A | 9/1999 | Besson | | 6,864,780 B2 | 3/2005 | Doi |
| 5,963,132 A * | 10/1999 | Yoakum .............. 340/572.1 | | 6,879,810 B2 | 4/2005 | Bouet |
| 5,974,124 A | 10/1999 | Schlueter, Jr. et al. | | 6,909,878 B2 | 6/2005 | Haller |
| 5,981,166 A | 11/1999 | Mandecki | | 6,922,592 B2 | 7/2005 | Thompson et al. |
| 5,999,846 A | 12/1999 | Pardey et al. | | 6,928,370 B2 | 8/2005 | Anuzis et al. |
| 6,038,464 A | 3/2000 | Axelgaard et al. | | 6,929,636 B1 | 8/2005 | Von Alten |
| 6,042,710 A | 3/2000 | Dubrow | | 6,937,150 B2 | 8/2005 | Medema |
| 6,047,203 A | 4/2000 | Sackner | | 6,942,616 B2 | 9/2005 | Kerr |
| 6,076,016 A | 6/2000 | Feierbach et al. | | 6,951,536 B2 | 10/2005 | Yokoi |
| 6,081,734 A | 6/2000 | Batz | | 6,957,107 B2 | 10/2005 | Rogers et al. |
| 6,091,975 A | 7/2000 | Daddona et al. | | 6,968,153 B1 | 11/2005 | Heinonen |
| 6,095,985 A | 8/2000 | Raymond et al. | | 6,987,965 B2 | 1/2006 | Ng et al. |
| 6,115,636 A | 9/2000 | Ryan | | 6,990,082 B1 | 1/2006 | Zehavi et al. |

| | | |
|---|---|---|
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,118,531 B2 | 10/2006 | Krill |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 * | 8/2008 | Kroll et al. .................. 340/573.1 |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 * | 9/2008 | Ayer et al. .................. 600/302 |
| 7,471,665 B2 | 12/2008 | Perlman |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,551,590 B2 | 6/2009 | Haller |
| 7,554,452 B2 | 6/2009 | Cole |
| 7,575,005 B2 | 8/2009 | Mumford |
| 7,616,111 B2 | 11/2009 | Covannon |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Cosentino |
| 7,756,587 B2 | 7/2010 | Penner et al. |
| 7,796,043 B2 * | 9/2010 | Euliano et al. .................. 340/573.1 |
| 7,797,033 B2 | 9/2010 | D'Andrea et al. |
| 7,809,399 B2 | 10/2010 | Lu |
| 7,844,341 B2 | 11/2010 | Von Arx et al. |
| 8,597,186 B2 | 12/2013 | Hafezi et al. |
| 2001/0027331 A1 | 10/2001 | Thompson |
| 2001/0044588 A1 | 11/2001 | Mault |
| 2001/0051766 A1 | 12/2001 | Gazdzinski |
| 2002/0002326 A1 | 1/2002 | Causey et al. |
| 2002/0026111 A1 | 2/2002 | Ackerman |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0132226 A1 | 9/2002 | Nair |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman |
| 2003/0023150 A1 | 1/2003 | Yokoi et al. |
| 2003/0028226 A1 | 2/2003 | Thompson |
| 2003/0065536 A1 | 4/2003 | Hansen |
| 2003/0076179 A1 | 4/2003 | Branch et al. |
| 2003/0083559 A1 | 5/2003 | Thompson |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |

| Publication No. | Date | Inventor |
|---|---|---|
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115517 A1 | 6/2004 | Fukada et al. |
| 2004/0121015 A1 | 6/2004 | Chidlaw et al. |
| 2004/0122297 A1 | 6/2004 | Stahmann et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167801 A1 | 8/2004 | Say et al. |
| 2004/0193020 A1 | 9/2004 | Chiba |
| 2004/0193029 A1 | 9/2004 | Glukhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1* | 10/2005 | Cole ............................ 600/420 |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0148339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1* | 12/2006 | Mercure et al. ............... 235/435 |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0014866 A1 | 1/2008 | Lipowshi |
| 2008/0020037 A1 | 1/2008 | Robertson et al. |
| 2008/0021519 A1 | 1/2008 | DeGeest |

| | | | | | | |
|---|---|---|---|---|---|---|
| 2008/0021521 A1 | 1/2008 | Shah | | 2009/0112626 A1 | 4/2009 | Talbot |
| 2008/0027679 A1 | 1/2008 | Shklarski | | 2009/0124871 A1 | 5/2009 | Arshak |
| 2008/0033273 A1 | 2/2008 | Zhou | | 2009/0131774 A1 | 5/2009 | Sweitzer |
| 2008/0039700 A1 | 2/2008 | Drinan et al. | | 2009/0135886 A1 | 5/2009 | Robertson et al. |
| 2008/0045843 A1 | 2/2008 | Tsuji et al. | | 2009/0157113 A1 | 6/2009 | Marcotte |
| 2008/0046038 A1 | 2/2008 | Hill | | 2009/0157358 A1 | 6/2009 | Kim |
| 2008/0051647 A1 | 2/2008 | Wu et al. | | 2009/0161602 A1 | 6/2009 | Matsumoto |
| 2008/0051667 A1 | 2/2008 | Goldreich | | 2009/0163789 A1 | 6/2009 | Say et al. |
| 2008/0058614 A1 | 3/2008 | Banet | | 2009/0171180 A1 | 7/2009 | Pering |
| 2008/0062856 A1 | 3/2008 | Feher | | 2009/0173628 A1 | 7/2009 | Say et al. |
| 2008/0065168 A1 | 3/2008 | Bitton et al. | | 2009/0177055 A1 | 7/2009 | Say et al. |
| 2008/0074307 A1 | 3/2008 | Boric-Lubecke | | 2009/0177056 A1 | 7/2009 | Say et al. |
| 2008/0077015 A1 | 3/2008 | Botic-Lubecke | | 2009/0177057 A1 | 7/2009 | Say et al. |
| 2008/0077028 A1 | 3/2008 | Schaldach et al. | | 2009/0177058 A1 | 7/2009 | Say et al. |
| 2008/0077188 A1 | 3/2008 | Denker et al. | | 2009/0177059 A1 | 7/2009 | Say et al. |
| 2008/0091089 A1 | 4/2008 | Guillory et al. | | 2009/0177060 A1 | 7/2009 | Say et al. |
| 2008/0091114 A1 | 4/2008 | Min | | 2009/0177061 A1 | 7/2009 | Say et al. |
| 2008/0097549 A1 | 4/2008 | Colbaugh | | 2009/0177062 A1 | 7/2009 | Say et al. |
| 2008/0097917 A1 | 4/2008 | Dicks | | 2009/0177063 A1 | 7/2009 | Say et al. |
| 2008/0103440 A1 | 5/2008 | Ferren et al. | | 2009/0177064 A1 | 7/2009 | Say et al. |
| 2008/0114224 A1 | 5/2008 | Bandy et al. | | 2009/0177065 A1 | 7/2009 | Say et al. |
| 2008/0119705 A1 | 5/2008 | Patel | | 2009/0177066 A1 | 7/2009 | Say et al. |
| 2008/0119716 A1 | 5/2008 | Boric-Lubecke | | 2009/0182206 A1 | 7/2009 | Najafi |
| 2008/0121825 A1 | 5/2008 | Trovato et al. | | 2009/0182212 A1 | 7/2009 | Say et al. |
| 2008/0137566 A1 | 6/2008 | Marholev | | 2009/0182213 A1 | 7/2009 | Say et al. |
| 2008/0139907 A1 | 6/2008 | Rao et al. | | 2009/0182214 A1 | 7/2009 | Say et al. |
| 2008/0140403 A1 | 6/2008 | Hughes et al. | | 2009/0182215 A1 | 7/2009 | Say et al. |
| 2008/0146871 A1 | 6/2008 | Arneson et al. | | 2009/0182388 A1 | 7/2009 | Von Arx |
| 2008/0146889 A1 | 6/2008 | Young | | 2009/0187088 A1 | 7/2009 | Say et al. |
| 2008/0146892 A1 | 6/2008 | LeBeouf | | 2009/0187089 A1 | 7/2009 | Say et al. |
| 2008/0154104 A1 | 6/2008 | Lamego | | 2009/0187090 A1 | 7/2009 | Say et al. |
| 2008/0166992 A1 | 7/2008 | Ricordi | | 2009/0187091 A1 | 7/2009 | Say et al. |
| 2008/0175898 A1 | 7/2008 | Jones et al. | | 2009/0187092 A1 | 7/2009 | Say et al. |
| 2008/0183245 A1 | 7/2008 | Van Oort | | 2009/0187093 A1 | 7/2009 | Say et al. |
| 2008/0188837 A1 | 8/2008 | Belsky et al. | | 2009/0187094 A1 | 7/2009 | Say et al. |
| 2008/0194912 A1 | 8/2008 | Trovato et al. | | 2009/0187095 A1 | 7/2009 | Say et al. |
| 2008/0208009 A1 | 8/2008 | Shklarski | | 2009/0187381 A1 | 7/2009 | King et al. |
| 2008/0214901 A1 | 9/2008 | Gehman | | 2009/0192351 A1 | 7/2009 | Nishino |
| 2008/0214985 A1 | 9/2008 | Yanaki | | 2009/0192368 A1 | 7/2009 | Say et al. |
| 2008/0243020 A1 | 10/2008 | Chou | | 2009/0192369 A1 | 7/2009 | Say et al. |
| 2008/0249360 A1 | 10/2008 | Li | | 2009/0192370 A1 | 7/2009 | Say et al. |
| 2008/0262320 A1 | 10/2008 | Schaefer et al. | | 2009/0192371 A1 | 7/2009 | Say et al. |
| 2008/0262336 A1 | 10/2008 | Ryu | | 2009/0192372 A1 | 7/2009 | Say et al. |
| 2008/0269664 A1 | 10/2008 | Trovato et al. | | 2009/0192373 A1 | 7/2009 | Say et al. |
| 2008/0275312 A1 | 11/2008 | Mosesov | | 2009/0192374 A1 | 7/2009 | Say et al. |
| 2008/0284599 A1 | 11/2008 | Zdeblick et al. | | 2009/0192375 A1 | 7/2009 | Say et al. |
| 2008/0288027 A1 | 11/2008 | Kroll | | 2009/0192376 A1 | 7/2009 | Say et al. |
| 2008/0294020 A1 | 11/2008 | Sapounas | | 2009/0192377 A1 | 7/2009 | Say et al. |
| 2008/0299197 A1 | 12/2008 | Toneguzzo et al. | | 2009/0192378 A1 | 7/2009 | Say et al. |
| 2008/0300572 A1 | 12/2008 | Rankers | | 2009/0192379 A1 | 7/2009 | Say et al. |
| 2008/0303638 A1 | 12/2008 | Nguyen | | 2009/0198115 A1 | 8/2009 | Say et al. |
| 2008/0306357 A1 | 12/2008 | Korman | | 2009/0198116 A1 | 8/2009 | Say et al. |
| 2008/0306359 A1 | 12/2008 | Zdeblick et al. | | 2009/0198175 A1 | 8/2009 | Say et al. |
| 2008/0306360 A1 | 12/2008 | Robertson et al. | | 2009/0203964 A1 | 8/2009 | Shimizu et al. |
| 2008/0311852 A1 | 12/2008 | Hansen | | 2009/0203971 A1 | 8/2009 | Sciarappa |
| 2008/0312522 A1 | 12/2008 | Rowlandson | | 2009/0203972 A1 | 8/2009 | Heneghan |
| 2008/0316020 A1 | 12/2008 | Robertson | | 2009/0203978 A1 | 8/2009 | Say et al. |
| 2009/0009330 A1 | 1/2009 | Sakama et al. | | 2009/0204265 A1 | 8/2009 | Hackett |
| 2009/0009332 A1* | 1/2009 | Nunez et al. ............... 340/572.1 | | 2009/0210164 A1 | 8/2009 | Say et al. |
| 2009/0024045 A1 | 1/2009 | Prakash | | 2009/0216101 A1 | 8/2009 | Say et al. |
| 2009/0030293 A1 | 1/2009 | Cooper et al. | | 2009/0216102 A1 | 8/2009 | Say et al. |
| 2009/0030297 A1 | 1/2009 | Miller | | 2009/0227204 A1 | 9/2009 | Robertson et al. |
| 2009/0034209 A1 | 2/2009 | Joo | | 2009/0227876 A1 | 9/2009 | Tran |
| 2009/0043171 A1 | 2/2009 | Rule | | 2009/0227940 A1 | 9/2009 | Say et al. |
| 2009/0048498 A1 | 2/2009 | Riskey | | 2009/0227941 A1 | 9/2009 | Say et al. |
| 2009/0062634 A1 | 3/2009 | Say et al. | | 2009/0227988 A1 | 9/2009 | Wood et al. |
| 2009/0062670 A1 | 3/2009 | Sterling | | 2009/0228214 A1 | 9/2009 | Say et al. |
| 2009/0069642 A1 | 3/2009 | Gao | | 2009/0231125 A1 | 9/2009 | Baldus |
| 2009/0069655 A1 | 3/2009 | Say et al. | | 2009/0234200 A1 | 9/2009 | Husheer |
| 2009/0069656 A1 | 3/2009 | Say et al. | | 2009/0243833 A1 | 10/2009 | Huang |
| 2009/0069657 A1 | 3/2009 | Say et al. | | 2009/0253960 A1 | 10/2009 | Takenaka et al. |
| 2009/0069658 A1 | 3/2009 | Say et al. | | 2009/0256702 A1 | 10/2009 | Robertson |
| 2009/0076343 A1 | 3/2009 | James | | 2009/0264714 A1 | 10/2009 | Chou |
| 2009/0082645 A1 | 3/2009 | Hafezi et al. | | 2009/0264964 A1 | 10/2009 | Abrahamson |
| 2009/0087483 A1 | 4/2009 | Sison | | 2009/0265186 A1 | 10/2009 | Tarassenko et al. |
| 2009/0088618 A1 | 4/2009 | Arneson | | 2009/0273467 A1 | 11/2009 | Elixmann |
| 2009/0099435 A1 | 4/2009 | Say et al. | | 2009/0281539 A1 | 11/2009 | Selig |
| 2009/0105561 A1 | 4/2009 | Boyden et al. | | 2009/0295548 A1 | 12/2009 | Ronkka |
| 2009/0110148 A1 | 4/2009 | Zhang | | 2009/0296677 A1 | 12/2009 | Mahany |

| Publication | Date | Inventor | | Country | Number | Date |
|---|---|---|---|---|---|---|
| 2009/0303920 A1 | 12/2009 | Mahany | | JP | 61072712 | 4/1986 |
| 2009/0306633 A1 | 12/2009 | Trovato et al. | | JP | 05-228128 | 9/1993 |
| 2009/0312619 A1 | 12/2009 | Say et al. | | JP | 2000-506410 | 5/2000 |
| 2009/0318303 A1 | 12/2009 | Delamarche et al. | | JP | 2002263185 | 9/2002 |
| 2009/0318761 A1 | 12/2009 | Rabinovitz | | JP | 2005-073886 | 3/2005 |
| 2009/0318779 A1 | 12/2009 | Tran | | JP | 2005-087552 | 4/2005 |
| 2009/0318783 A1 | 12/2009 | Rohde | | JP | 2005-304880 | 4/2005 |
| 2009/0318793 A1 | 12/2009 | Datta | | JP | 2006006377 | 1/2006 |
| 2010/0001841 A1 | 1/2010 | Cardullo | | JP | 2006509574 | 3/2006 |
| 2010/0010330 A1 | 1/2010 | Rankers | | JP | 2007-313340 | 12/2007 |
| 2010/0033324 A1 | 2/2010 | Shimizu et al. | | JP | 2008011865 | 1/2008 |
| 2010/0049004 A1 | 2/2010 | Edman et al. | | KR | 2006077523 | 7/2006 |
| 2010/0049006 A1 | 2/2010 | Magar | | WO | WO8802237 | 4/1988 |
| 2010/0049012 A1 | 2/2010 | Dijksman et al. | | WO | WO9221307 | 12/1992 |
| 2010/0049069 A1 | 2/2010 | Tarassenko et al. | | WO | WO9308734 | 5/1993 |
| 2010/0056878 A1 | 3/2010 | Partin | | WO | WO9319667 | 10/1993 |
| 2010/0056891 A1 | 3/2010 | Say et al. | | WO | WO9739963 | 10/1997 |
| 2010/0056939 A1 | 3/2010 | Tarassenko et al. | | WO | WO9843537 | 10/1998 |
| 2010/0057041 A1 | 3/2010 | Hayter | | WO | WO9937290 | 7/1999 |
| 2010/0062709 A1 | 3/2010 | Kato | | WO | WO9959465 | 11/1999 |
| 2010/0063438 A1 | 3/2010 | Bengtsson | | WO | WO0033246 | 6/2000 |
| 2010/0063841 A1 | 3/2010 | D'Ambrosia et al. | | WO | WO0147466 | 7/2001 |
| 2010/0069002 A1 | 3/2010 | Rong | | WO | WO0174011 | 10/2001 |
| 2010/0069717 A1 | 3/2010 | Hafezi et al. | | WO | WO0180731 | 11/2001 |
| 2010/0081894 A1 | 4/2010 | Zdeblick et al. | | WO | WO0245489 | 6/2002 |
| 2010/0099967 A1 | 4/2010 | Say et al. | | WO | WO02058330 | 7/2002 |
| 2010/0099968 A1 | 4/2010 | Say et al. | | WO | WO02062276 | 8/2002 |
| 2010/0099969 A1 | 4/2010 | Say et al. | | WO | WO02087681 | 11/2002 |
| 2010/0100077 A1 | 4/2010 | Rush | | WO | WO02095351 | 11/2002 |
| 2010/0100078 A1 | 4/2010 | Say et al. | | WO | WO03050643 | 6/2003 |
| 2010/0106001 A1 | 4/2010 | Say et al. | | WO | WO03068061 | 8/2003 |
| 2010/0118853 A1 | 5/2010 | Godfrey | | WO | WO2004014225 | 2/2004 |
| 2010/0139672 A1 | 6/2010 | Kroll et al. | | WO | WO2004019172 | 3/2004 |
| 2010/0168659 A1 | 7/2010 | Say et al. | | WO | WO2004039256 | 5/2004 |
| 2010/0179398 A1 | 7/2010 | Say et al. | | WO | WO2004059551 | 7/2004 |
| 2010/0185055 A1 | 7/2010 | Robertson | | WO | WO2004066833 | 8/2004 |
| 2010/0191073 A1 | 7/2010 | Tarassenko et al. | | WO | WO2004066834 | 8/2004 |
| 2010/0210299 A1 | 8/2010 | Gorbachov | | WO | WO2004066903 | 8/2004 |
| 2010/0222652 A1 | 9/2010 | Cho | | WO | WO2004068881 | 8/2004 |
| 2010/0228113 A1 | 9/2010 | Solosko | | WO | WO2004109316 | 12/2004 |
| 2010/0233026 A1 | 9/2010 | Ismagiov et al. | | WO | WO2005011237 | 2/2005 |
| 2010/0234706 A1 | 9/2010 | Gilland | | WO | WO2005020023 | 3/2005 |
| 2010/0234715 A1 | 9/2010 | Shin | | WO | WO2005024687 | 3/2005 |
| 2010/0234914 A1 | 9/2010 | Shen | | WO | WO2005024837 | 5/2005 |
| 2010/0239616 A1 | 9/2010 | Hafezi et al. | | WO | WO2005051166 | 6/2005 |
| 2010/0245091 A1 | 9/2010 | Singh | | WO | WO2005083621 | 9/2005 |
| 2010/0249881 A1 | 9/2010 | Corndorf | | WO | WO2005110238 | 11/2005 |
| 2010/0256461 A1 | 10/2010 | Mohamedali | | WO | WO2006021932 | 3/2006 |
| 2010/0259543 A1 | 10/2010 | Tarassenko et al. | | WO | WO2006027586 | 3/2006 |
| 2010/0268048 A1 | 10/2010 | Say et al. | | WO | WO2006046648 | 5/2006 |
| 2010/0268049 A1 | 10/2010 | Say et al. | | WO | WO2006055892 | 5/2006 |
| 2010/0268050 A1 | 10/2010 | Say et al. | | WO | WO2006055956 | 5/2006 |
| 2010/0274111 A1 | 10/2010 | Say et al. | | WO | WO2006075016 | 7/2006 |
| 2010/0280345 A1 | 11/2010 | Say et al. | | WO | WO2006100620 | 9/2006 |
| 2010/0280346 A1 | 11/2010 | Say et al. | | WO | WO2006116718 | 11/2006 |
| 2010/0295694 A1 | 11/2010 | Kauffman et al. | | WO | WO2006127355 | 11/2006 |
| 2010/0298668 A1 | 11/2010 | Hafezi et al. | | WO | WO2007001724 | 1/2007 |
| 2010/0298730 A1 | 11/2010 | Tarassenko et al. | | WO | WO2007001742 | 1/2007 |
| 2010/0312188 A1 | 12/2010 | Robertson et al. | | WO | WO2007013952 | 2/2007 |
| 2010/0312580 A1 | 12/2010 | Tarassenko et al. | | WO | WO2007014084 | 2/2007 |
| 2011/0009715 A1 | 1/2011 | O'Reilly et al. | | WO | WO2007014527 | 2/2007 |
| 2011/0054265 A1 | 3/2011 | Hafezi et al. | | WO | WO2007021496 | 2/2007 |
| 2011/0065983 A1 | 3/2011 | Hafezi et al. | | WO | WO2007027660 | 3/2007 |
| 2011/0077660 A1 | 3/2011 | Janik et al. | | WO | WO2007028035 | 3/2007 |
| 2011/0105864 A1 | 5/2011 | Robertson et al. | | WO | WO2007036687 | 4/2007 |
| 2011/0124983 A1 | 5/2011 | Kroll et al. | | WO | WO2007036741 | 4/2007 |
| 2011/0224912 A1 | 9/2011 | Bhavaraju et al. | | WO | WO2007036746 | 4/2007 |
| 2011/0230732 A1 | 9/2011 | Edman et al. | | WO | WO2007040878 | 4/2007 |
| 2012/0059257 A1 | 3/2012 | Duck et al. | | WO | WO2007067054 | 6/2007 |
| 2012/0062371 A1 | 3/2012 | Radivojevic et al. | | WO | WO2007071180 | 6/2007 |
| | | | | WO | WO2007096810 | 8/2007 |
| FOREIGN PATENT DOCUMENTS | | | | WO | WO2007101141 | 9/2007 |
| | | | | WO | WO2007115087 | 10/2007 |
| EP | 0344939 | 12/1989 | | WO | WO2007120946 | 10/2007 |
| EP | 1246356 | 10/2002 | | WO | WO2007127316 | 11/2007 |
| EP | 1534054 | 5/2005 | | WO | WO2007127879 | 11/2007 |
| EP | 1702553 | 9/2006 | | WO | WO2007128165 | 11/2007 |
| EP | 1789128 | 5/2007 | | WO | WO2007130491 | 11/2007 |
| EP | 2143369 | 1/2010 | | WO | WO2007143535 | 12/2007 |

| | | |
|---|---|---|
| WO | WO2007149546 | 12/2007 |
| WO | WO2006104843 | 1/2008 |
| WO | WO2008008281 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009006615 | 1/2009 |
| WO | WO2009029453 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010000085 | 1/2010 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |

OTHER PUBLICATIONS

Gaglani S. "Put Your Phone, Or Skin, on Vibrate" MedGadget (2012) http://medgadget.com/2012/03/put-your-phone-or-skin-on-vibrate.html 8pp.
Jung, S. "Dissolvable 'Transient Electronics' Will Be Good for Your Body and the Environment" MedGadget; Oct. 1 (2012); Online website: http://medgadget.com/2012/10/dissolvable-transient-electronics-will-be-good-for-your-body-and-the-environment.html; downloaded Oct. 24, 2012; 4 pp.
Rolison et al., "Electrically conductive oxide aerogels: new materials in electrochemistry" J. Mater. Chem. (2001) 1, 963-980.
AADE, "AADE 37th Annual Meeting San Antonio Aug 4-7 2010" American Association of Diabetes Educators (2010); http://www.diabeteseducator.org/annualmeeting/2010/index.html; 2 pp.
Arshak et al., A Review and Adaptation of Methods of Object Tracking to Telemetry Capsules IC-Med (2007) vol. 1, No. 1, Issue 1, pp. 35 of 46.
"ASGE Technology Status Evaluation Report: wireless capsule endoscopy" American Soc. For Gastrointestinal Endoscopy (2006) vol. 63, No. 4; 7 pp.
Aydin et al., "Design and implementation considerations for an advanced wireless interface in miniaturized integrated sensor Microsystems" Sch. of Eng. & Electron., Edinburgh Univ., UK; (2003); abstract.
Barrie, Heidelberg pH capsule gastric analysis. Texbook of Natural Medicine, (1992), Pizzorno, Murray & Barrie.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf.

Carlson et al., "Evaluation of a non-invasive respiratory monitoring system for sleeping subjects" Physiological Measurement (1999) 20(1): 53.
Coury, L. "Conductance Measurement Part 1: Theory"; Current Separations, 18:3 (1999) p. 91-96.
Delvaux et al., "Capsule endoscopy: Technique and indications" Clinical Gastoenterology (2008) vol. 22, Issue 5, pp. 813-837.
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Fawaz et al., "Enhanced Telemetry System using CP-QPSK Band—Pass Modulation Technique Suitable for Smart Pill Medical Application" IFIP IEEE Dubai Conference (2008); http://www.asic.fh-offenburg.de/downloads/ePille/IFIP_IEEE_Dubai_Conference.pdf.
Ferguson et al., "Dialectric Constant Studies III Aqueous Gelatin Solutions" J. Chem. Phys. 2, 94 (1934) p. 94-98.
Furse C. M., "Dipole Antennas" J. Webster (ed). Wiley Encyclopedia of Electrical and Electronics Engineering (1999) p. 575-581.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12): 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.
ISFET—Ion Sensitive Field-Effect Transistor; MICROSENS S.A. pdf document. First cited by Examiner in Office Action dated Jun. 13, 2011 for U.S. Appl. No. 12/238,345; 4pp.
Intromedic, MicroCam Innovative Capsule Endoscope Pamphlet. (2006) 8 pp (http://www.intromedic.com/en/product/productinfo.asp).
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink (2010) 2 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
Mackay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
Medtronic, "CareLink Therapy Management Software for Diabetes" (2010); https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" (2010) http://www.medtronicdiabetes.com/products/index.html; 2 pp.
Medtronic, "Mini Med Paradigm ® Revel ™ Insulin Pump" (2010) http://www.medtronicdiabetes.com/products/insulinpumps/index.html; 2 pp.

Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget (2008); http://www.engadget.com/2008/07/29/walkers-swallow-rfid-pills-for-science/.
Minimitter Co. Inc. "Actiheart" Traditional 510(k) Summary. Sep. 27, 2005.
Minimitter Co. Inc. Noninvasive technology to help your studies succeed. Mini Mitter.com Mar. 31, 2009.
Mini Mitter Co, Inc. 510(k) Premarket Notification Mini-Logger for Diagnostic Spirometer. 9-21 (1999).
Mini Mitter Co, Inc. 510(k) Premarket Notification for VitalSense. Apr. 22, 2004.
Minimitter Co. Inc. VitalSense Integrated Physiological Monitoring System. Product Description. (2005).
Minimitter Co. Inc. VitalSense Wireless Vital Signs Monitoring. Temperatures.com Mar. 31, (2009).
Mohaverian et al., "Estimation of gastric residence time of the Heidelberg capsule in humans: effect of varying food composition" Gastroenterology (1985) 89:(2): 392-7.
"New 'smart pill' to track adherence" E-Health-lnsider (2010) http://www.e-health-insider.com/news/5910/new_'smart pill'_monitors_medicines.
NPL_AntennaBasics.pdf, Radio Antennae, http://www.erikdeman.de/html/sail018h.htm; (2008) 3pp.
O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Philips Respironics (http/minimitter.com/products.cfm) Products, Noninvasive Technology to Help Your Studies Succeed. 510(k) Permanent Notification for Vital Sense. Apr. 22, 2004.
"RFID pill monitors marchers" RFID News (2008) http://www.rfidnews.org/2008/07/23/rfid-pill-monitors-marchers/.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. (2009) 28pp.; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics-Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010).
"Smartlife awarded patent for knitted transducer" Innovation in Textiles News: http://www.innovationintextiles.com/articles/208.php; 2pp. (2009).
"The SmartPill Wireless Motility Capsule" Smartpill, The Measure of GI Health; (2010) http://www.smartpillcorp.com/index.cfm?pagepath=Products/The_SmartPill_Capsule&id=17814.
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal (2010) Apr. 27th; http://www.rfidjournal.com/article/view/7560/1.

Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
University of Florida News "Rx for health: Engineers design pill that signals it has been swallowed" (2010) 2pp.; http://news.ufl.edu/2010/03/31/antenna-pill-2/.
U.S. Appl. No. 12/238,345, filed Sep. 25, 2008, Hooman et al., Non-Final Office Action mailed Jun. 13, 2011 22pp.
Walkey, "MOSFET Structure and Processing"; 97.398 Physical Electronics.
Lecture 20; First cited by Examiner in Office Action dated Jun. 13 (2011) for U.S. Appl. No. 12/238,345; 24 pp.
Watson, et al., "Determination of the relationship between the pH and conductivity of gastric juice" Physiol Meas. 17 (1996) pp. 21-27.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Yao et al., "Low Power Digital Communication in Implantable Devices Using Volume Conduction of Biological Tissues" Proceedings of the 28th IEEE, EMBS Annual International Conference, Aug. 30-Sep. 3, 2006
Zimmerman, "Personal Area Networks: Near-field intrabody communication" IBM Systems Journal (1996) 35 (3-4):609-17.
Description of ePatch Technology Platform for ECG and EMG, located it http://www.madebydelta.com/imported/images/DELTA_Web/documents/ME/ePatch_ECG_EMG.pdf, Dated Sep. 2, 2010.
Zworkin, "A Radio Pill" Nature, (1957) 898, 179 Nature Publishing Group.
Trutag, Technologies, Inc., Spectral Microtags for Authentication and Anti-Counterfeiting; "Product Authentication and Brand Protection Solutions"; http://www.trutags.com/; downloaded Feb. 12, 2013; 1 pp.
Winter, J. et al. "The material properties of gelatin gels"; USA Ballistic Research Laboratories, Mar. 1975, p. 1-157.

* cited by examiner

*Primary Examiner* — Bill Thomson
*Assistant Examiner* — Marie Archer
(74) *Attorney, Agent, or Firm* — Bozicevic, Field & Francis LLP; Bret E. Field

(57) ABSTRACT

A system and method are provided for securing an ingestible electronic device to a pharmaceutical product without damaging the ingestible electronic device. The product includes the ingestible electronic device being placed on the product in accordance with one aspect of the present invention. In accordance with another aspect of the present invention, the ingestible electronic device is placed inside the product. Various embodiments are disclosed in accordance with the present invention for protecting and/or coating of the electronic marker as well as securing the ingestible electronic device onto the product.

12 Claims, 14 Drawing Sheets

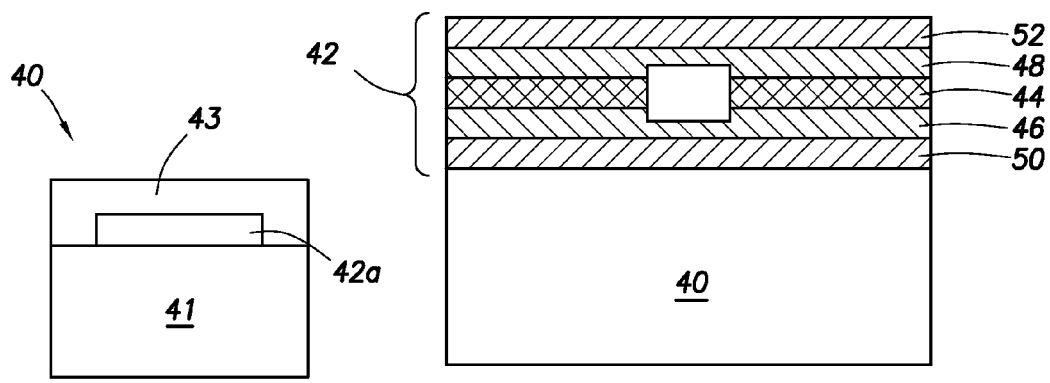
FIG.3B          FIG.3A
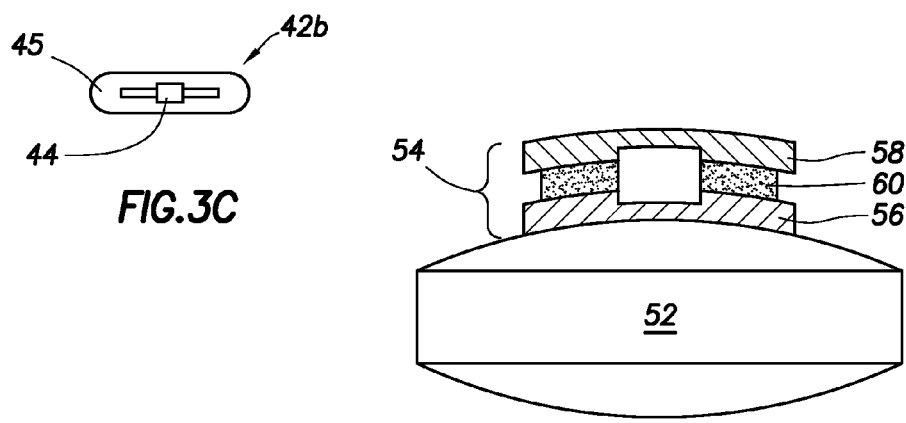
FIG.3C
FIG.4
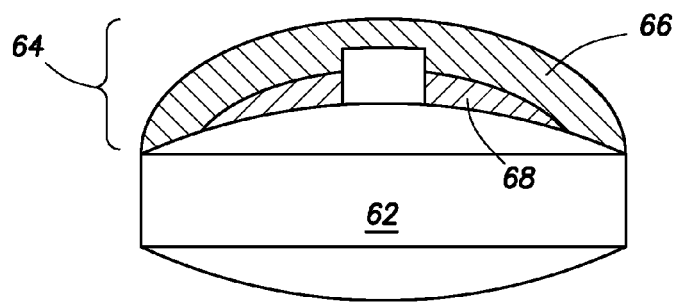
FIG.5

INTEGRATED INGESTIBLE EVENT MARKER SYSTEM WITH PHARMACEUTICAL PRODUCT

CROSS-REFERENCE AND RELATED APPLICATION

Pursuant to 35 U.S.C. §119 (e), this application claims priority to the filing date of U.S. Provisional Patent Application Ser. No. 61/266,103 filed on Dec. 2, 2009 and titled INTEGRATED INGESTIBLE EVENT MARKER SYSTEM WITH PHARMACEUTICAL PRODUCT, the disclosure of which application is incorporated herein by reference.

This application is related to and incorporates by reference the following applications: U.S. Provisional Application Ser. No. 61/416,150 field on Nov. 22, 2010 and titled INGESTIBLE DEVICE WITH PHARMACEUTICAL PRODUCT; U.S. application Ser. No. 12/447,172 filed on Oct. 25, 2007 and titled CONTROLLED ACTIVATION INGESTIBLE IDENTIFIER; U.S. Provisional Application 60/862,925 filed on Oct. 25, 2006 and titled CONTROLLED ACTIVATION PHARMA-INFORMATICS SYSTEM; PCT Application US2007/82563 and filed on Oct. 25, 2007 and titled CONTROLLED ACTIVATION INGESTIBLE IDENTIFIER.

FIELD OF INVENTION

The present invention relates to electronic devices with partial power sources and, more specifically, to electronic devices secured to a pharmaceutical product wherein the electronic devices are activated upon contact with a conducting fluid.

BACKGROUND

Pharmaceutical products are delivered to a user in many forms, including a pill. Integration of a pharmaceutical product with an ingestible device is often a challenge due to the delicate nature of the electronic components as well as the difficulty in securing the electronic components to the pharmaceutical product, such as a pill or tablet or capsule. For example, tablets are typically made using a press that applies pressure to a powder form. The pressures produced by the press can often damage the electronic components that are placed inside the tablet or pill. Additionally, securing the electronic component to the surface of tablet using adhesive material often results in damage to the device caused by the adhesive, which may be a thermally or chemically activated type of adhesive. Furthermore, handling a small electronic device is often a challenge during the assembly process. Therefore, what is needed is a system and method for securing an ingestible electronic device to a pharmaceutical product without damaging the ingestible electronic device.

SUMMARY

The present invention provides a system and method for securing an ingestible electronic device to a pharmaceutical product without damaging the ingestible electronic device. The product includes an electronic marker placed on the product in accordance with one aspect of the present invention. In accordance with another aspect of the present invention, the electronic marker is placed inside the product. Various embodiments are disclosed in accordance with the present invention that allow for protection and coating of the electronic marker.

DESCRIPTION OF THE DRAWINGS

FIG. 3A shows a tablet with a device assembly secured on one surface in accordance with one aspect of the present invention.

FIG. 3B shows a first tablet portion with a device assembly secured on one surface and a second tablet portion secured over the device assembly in accordance with one aspect of the present invention.

FIG. 3C shows a device assembly with a laminated coating in accordance with one aspect of the present invention.

FIG. 4 shows a tablet with a device assembly secured on one surface in accordance with one aspect of the present invention.

FIG. 5 shows a tablet with a device assembly secured on one surface in accordance with one aspect of the present invention.

DETAILED DESCRIPTION

The present invention discloses multiple approaches to securing a device capable of indicating the occurrence of an event, such as ingestion, to an ingestible product, such as a pharmaceutical product in the form of a pill or tablet. In order to better understand the process and systems involved the systems are described in greater detail with respect to the devices being secured within the product as well as the devices being secured onto the product's outer surface. For example, the process of securing the device onto the product may be done using pressure, temperature, chemical reactions or a combination thereof. In accordance with one aspect of the present invention, the device is protected from these conditions through the various securing layers and protective layers disclosed herein. The materials used are effective in temperature ranges are 25-200 degrees Celsius, including a target range of 80-150 degrees Celsius and the duration of exposure time to such temperatures. The exposure times will vary from 0.1 sec to 50 sec, including a target range of 1 sec to 15 sec. Additionally, the device will be protected from forces involved, which range from 1 to 50 pounds, including 2-8 pounds, as well the pressures exerted during integration of the device with the pill, which pressures range from 100-400 PSI. Thus, the scope of the present invention includes use of materials to protect the device and product from the various environmental parameters (such as pressure, time, forces, chemical reactions, and combinations thereof) associated with the integration of the device with the pill.

Furthermore, the scope of the present invention is not limited by the shape or type of product. For example, the product can be a pill, including capsule, a time-release oral dosage, a tablet, a gel capsule, a sub-lingual tablet or any oral dosage product. A pill may contain or be made of any of the following, alone or in combination: an active agent, a drug, a placebo, vitamins, or any food material. In accordance with one aspect of the present invention, the product has the device positioned inside or secured to the interior of the product. In an alternative arrangement, the device is secured to the exterior of the product.

Figure 1:
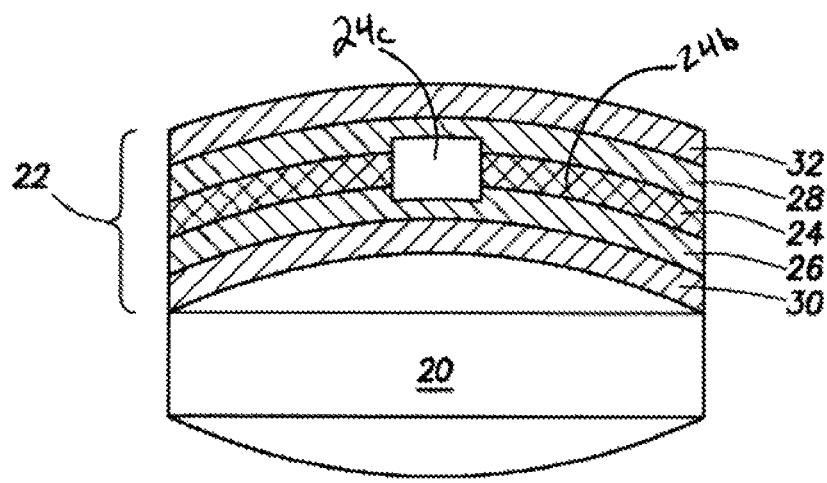
FIG. 1 shows a tablet with a device assembly secured on one surface in accordance with one aspect of the present invention.
Figure 2:
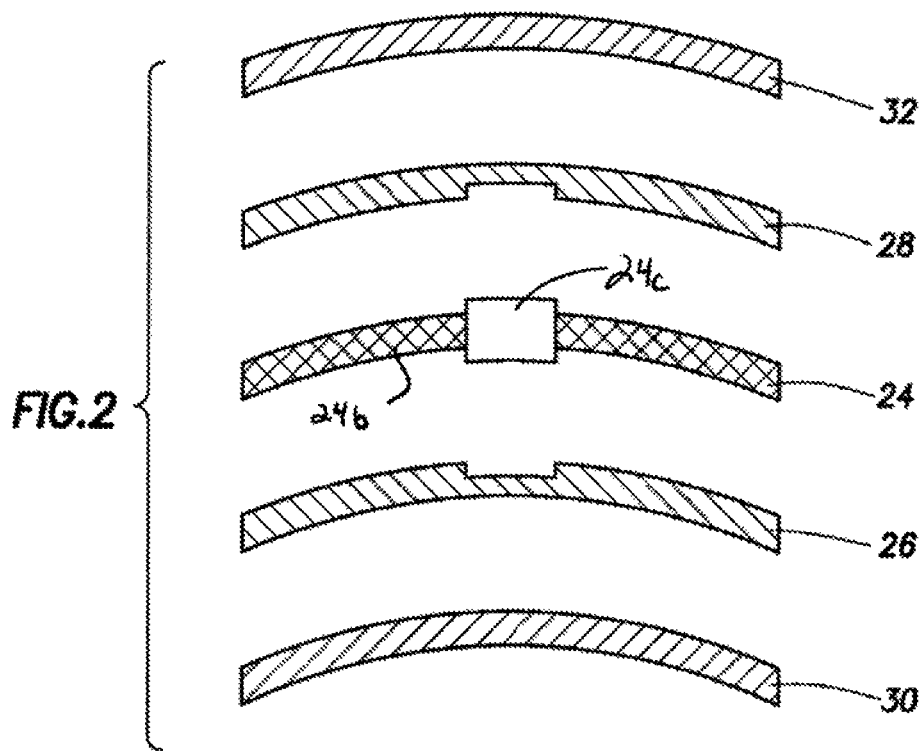
FIG. 2 is an exploded view of the device assembly of FIG. 1.
Figure 1A:
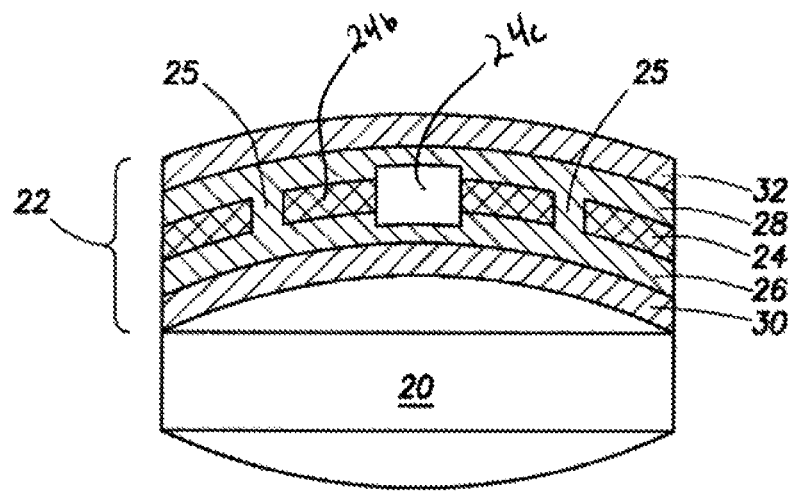
FIG. 1A shows a tablet with a device assembly secured on one surface in accordance with one aspect of the present invention.
Figure 2A:
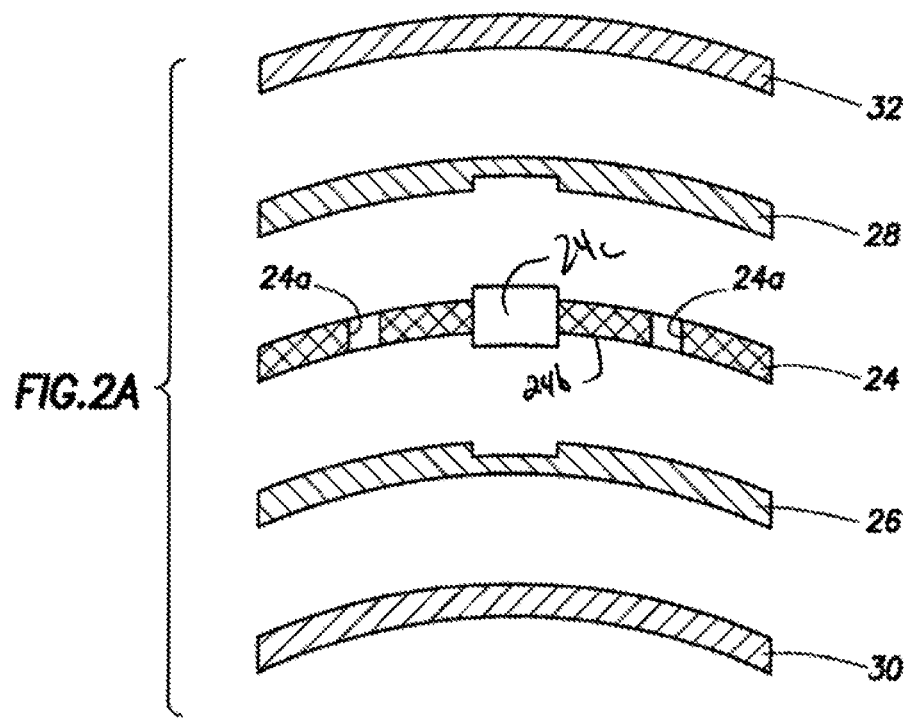
FIG. 2A is an exploded view of the device assembly of FIG. 1A.

Referring now to FIG. 1, an example of a pill 20 having a convex surface is shown with a marker assembly 22 secured on the outside. Additionally, the marker assembly 22 conforms to the shape of the pill 20. In the current example, as shown in FIG. 2, the marker assembly 22 includes an ingestible event marker or an ionic emission module (IEM) unit 24, a lower protective layer 26, an upper protective layer 28, an adhesive or securing layer 30, and a decorative or printing layer 32. In accordance with one aspect of the present invention, a non-conduction outer portion or skirt 24b of the IEM unit 24 includes holes 24a, as shown in FIG. 2A distributed around the IEM unit 24 so that layers 26 and 28 maybe laminated together at connection 25, as shown in FIG. 1A, through the holes 24a as the layers 26 and 28 are secured to or laminated onto the IEM unit 24.

Figure 1B:
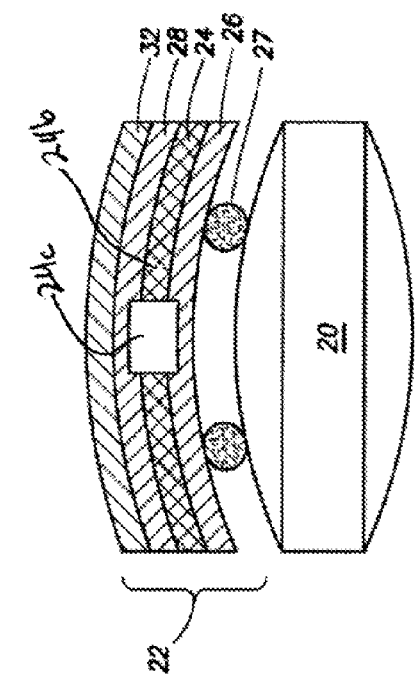
FIG. 1B shows a tablet with a device assembly secured on one surface in accordance with one aspect of the present invention.
Figure 1C:
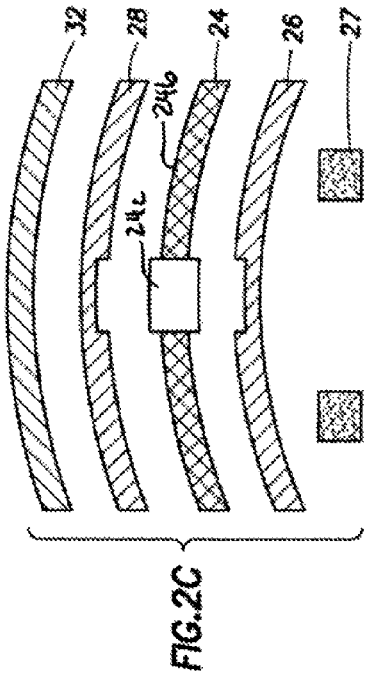
FIG. 1C shows a tablet with a device assembly secured on one surface in accordance with one aspect of the present invention.
Figure 2B:
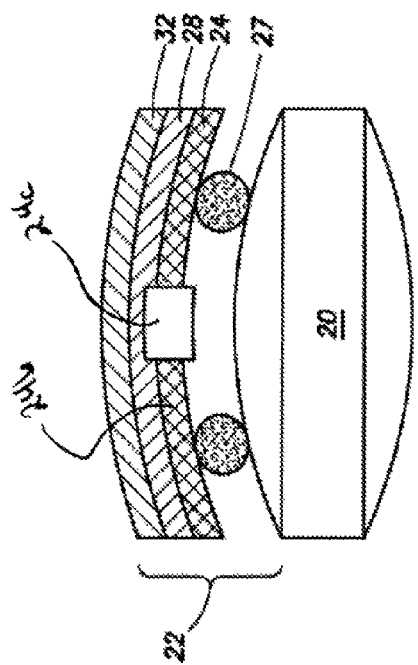
FIG. 2B is an exploded view of the device assembly of FIG. 1B.
Figure 2C:
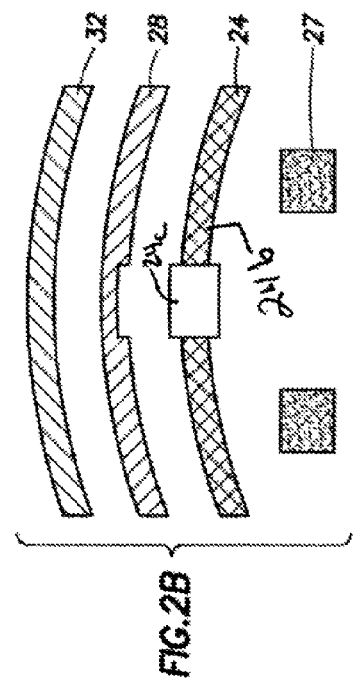
FIG. 2C is an exploded view of the device assembly of FIG. 1B.

Referring now to FIGS. 1B and 2B, in accordance with another aspect of the present invention, the protective player 26 and the securing layer 30 of FIG. 1 are preplaced by a plurality of securing dots or portions 27. As shown in FIGS. 1 and 2C, in accordance with another aspect of the present invention, the protective layer 26 is included and the securing layer 30 of FIG. 1 is preplaced by a plurality of securing dots or portions 27. The marker assembly 22 is separated from the pill 20 by an air gap and, hence, able to be secured to the pill 20 regardless of the shape of the pill 20 since the dots 27 deform and adjust to contour to the shape of the pill 20. Thus, when the shape of the pill 20 is such that the marker assembly 22 cannot be easily conformed to the shape of the pill 20, the dots 27 will deform and adapt. This ensures a secure connection between the shape of the pill 20 and the shape of the marker assembly 22. The dots 27 are distributed about the marker assembly 22 and used to connect the marker assembly 22 to the pill 20. Furthermore, the thickness or amount of securing materials needed to secure each marker assembly 22 to the pill 20 would be reduced.

The IEM unit 24 includes a control unit 24c surrounded by the skirt 24b and two dissimilar materials (not shown), each of which dissimilar material is electrically connected to the control unit 24c and isolated from each other. The dissimilar materials represent a portion of a power source or may be referred to as a partial power source and when in contact with a conducting fluid, produce a voltage potential across the materials as the materials dissolve. Once the IEM unit 24 comes into contact with a conducting fluid, such as body fluids found in the stomach, then the IEM unit 24 is activated and a current flow is produced by the dissimilar materials dissolving into solution and the voltage potential is produced between the dissimilar materials as they go from solid state to solution.

According to another aspect of the present invention, the securing layer 30 may also be replaced by a layer that includes the properties of adhesion and releasing. For example, the release functionality is achieved by incorporating a disintegrant (e.g. Sodium starch glycolate) or water soluble excipient (e.g. Hydroxypropyl cellulose). Thus, then when the assembly 22 gets wet, the layer 30 would eject the marker assembly 22 from the pill 20. Accordingly, to the extent that reference is made in the present invention to an adhesive or securing layer, the scope of the present invention contemplates the use of either a layer that has adhesive properties or a layer that has both adhesive and releasing properties. The scope of the present invention is not limited by the shape of the marker assembly 22. The IEM concept can be expanded to a "galvanic tablet" or dosage form where the drug release rate is galvanically controlled by an integrated circuit (IC). The dosage form would consist of a chip, connected to a partial power source (e.g. a CuCl—Mg materials similar to the material used with IEM), and also connected to a matrix containing a drug compound. Once activated, the IC controls the rate of drug discharge by controlling the current or potential applied to the matrix. An example of this is a matrix consisting of a drug compound, a binder, and an electrochemically soluble material, e.g., a salt. Electrochemical conversion of the salt to a soluble species erodes or creates pores in the matrix that releases the drug at a precise rate corresponding to the charge passed.

The IC can control the charge applied to the matrix at any desirable rate, e.g., to achieve constant drug discharge, pulsatile discharge, gradually ramped drug delivery. Discharge can be in response to a physiological signal sensed by the IC, e.g., local pH, impedance, motility, location in the GI tract, bleeding. Discharge can also be externally triggered, e.g. the IC may contain an RF antenna that allows the patient or a medical monitor, e.g. personal health companion, blood monitor, to set off drug release in response to a physical condition like pain. IEM configurations of interest include, but are not limited to: those described in: PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; PCT application serial no. PCT/US2008/077753 published as WO 2009/042812; U.S. patent application Ser. No. 12/546,017; and U.S. Provisional Application Ser. Nos. 61/142,849; 61/142,861; 61/173,511; 61/173,564; and 61/177,611; the disclosures of which applications are herein incorporated by reference.

The dosage form is capable of providing very precise drug concentrations in the blood, rapid dose delivery for pain management, or localized delivery in the GI tract. Medical applications may include GI disease, e.g., motility, colitis, pain management, localized delivery to tumors, customized dosing of therapeutics, e.g., immunosuppressants, and others.

Other release mechanisms are also possible: the drug matrix may contain an electroactive drug-binding polymer, e.g. Nafion, proteins, whose state of charge or degree of swelling can be altered by application of a current or potential. Application of a potential by the IC alters the binding properties of the polymer to the drug to effectuate release of the drug. Another possible mechanism is that the IC controls the concentration of a solution species around the dosage form, e.g. H+, which in turn can increase/decrease the solubility of the drug matrix and modulate drug release. The current may also be applied to an outer layer of the dosage form rather than the entire matrix to control the dissolution rate of a coating.

The power source and the drug matrix can be distinct or the same. For example, a matrix may contain CuCl as the electrochemically active species. CuCl can act both as a cathode to power the IC and as a species whose conversion (to copper and chloride ions) releases the drug. The IC location may be in the bulk of the dosage form or on the surface. The sensors can be incorporated into the IC and used to trigger drug release or report physiological conditions to a receiver unit, e.g., pH, impedance, chemical sensor, temperature (detect bleeding). The sheath, coating, or manifold may be used to confine the matrix so that dissolution occurs only at one surface while the other surfaces are coated by a sheath that prevents dissolution. A coating may also be applied to prevent drug release until the drug reaches a desired location in the GI tract, e.g. intestine or colon.

One example of a pain management scenario is that there is usually a basal rate of pain relief from a long-acting opioid (e.g., Oxycontin) coupled with self-titrated short-acting opioid for breakthrough pain. This paradigm is used for both injectable and oral regimens. This invention could handle both basal and breakthrough pain in the same pill or cluster of pills, or one could use the invention solely for the breakthrough component, if the patient were also taking a standard long-acting oral agent. This relates to conceiving of this as an Ingestible Patient-Controlled Analgesia system (analogous to the in-hospital, IV-based PCA). One aspect of the present invention includes stably associating the IEM with a pharmaceutically inactive excipient material designed to: 1) protect the IEM from moisture, handling and the nearby environment; and 2) protect the active pharmaceutical elsewhere in the formulation from damage or degradation by the IEM itself. One or more protective IEM "sandwiches" could be developed such that the final IEM plus excipient module could be reliably integrated into the final tablet or capsule oral dosage form with minimal risk of deleterious effects on product dissolution or stability. Over time, once characterization of IEM sandwich performance has been completed in association with active pharmaceuticals bracketing the range of essential drug characteristics, e.g., pH, dissolution, bioavailability, solubility, regulatory clearance-related testing of an IEM-enabled medication might be streamlined, leading to a quicker time-to-market for what would in essence become a new form of proprietary medication, one where the market exclusivity would not necessarily depend upon the molecular composition-of-matter patent, but on the incorporation of the IEM and the attendant capabilities enabled by such incorporation.

Referring now to FIG. 3A, a pill 40 having a near planar or flat surface is shown with a marker assembly 42 secured on the outside. The marker assembly 42 conforms to the shape of the pill 40. In the current example, the marker assembly 42 includes an IEM unit 44, a lower protective layer 46, an upper protective layer 48, an adhesive or securing layer 50 and a decorative or printing layer 52.

Referring now the FIG. 3B, in accordance with another aspect of the present invention, the pill 40 is shown with a first tablet portion 41. A marker assembly 42a is shown secured to the surface of the first tablet portion 41. The marker assembly 42a is covered by a second tablet portion 43. The portion 41 and the portion 43 may be similar or different materials. For example, in accordance with one aspect of the present invention, the portion 41 may be the drug product and the portion 43 may be fast dissolving material. The marker assembly 42a may be similar to the marker assembly 42 of FIG. 3A or it may simply be just the IEM unit 44 with the lower layer 46 and the upper layer 48.

Referring now to FIG. 3B and FIG. 3C, in accordance with another aspect of the present invention, the marker assembly 42a may be replaced by the marker assembly 42b of FIG. 3C. The marker assembly 42B includes the IEM unit 44 and a lamination or film coating 45. The laminated layer is made of a dissolvable material that delays the activation of the IEM unit 44 once the portion 41 and portion 43 of the pill 40 have dissolved or disintegrated to release the marker assembly 42b. The film coating 45 may be made of a variety of materials or films, such as polymer films, including polyethylene oxide, hydroxypropyl cellulose, and triethyl citrate. Other films that can be used include any dissolvable polymer or plasticizer. The film coating 45 provides a moisture barrier and dissolves under the proper conditions to delay activation of the IEM unit 44. The film coating 45 is designed to provide sufficient delay in exposure of the IEM unit to the surrounding fluids relative to the disintegration and dispersion of the pill 40. The film coating 45 may include any of the following: soluble materials, barrier materials (such as lipids, polyvinyl alcohol), processing aids (such as plasticizers, adhesion promoters), and stabilizers. Furthermore, the film coating 45 may be manufactured via lamination, application of a coating solution or slurry followed by a cure. For example, in accordance with one aspect of the present invention, the film coating 44 may be laminated to the IEM unit 44, wherein the edge or extremities of the IEM unit 44 are exposed as shown in FIG. 3A. For example, in accordance with another aspect of the present invention, the film coating 44 may be laminated around the IEM unit 44 to form a pocket, wherein the edge or extremities of the IEM unit 44 are covered as shown in FIG. 3B. In accordance with other aspects of the present invention, the film coating 45 may be formed around the IEM unit 44 using dry compression, such as a tablet press.

It will also be apparent that the various layers disclosed can be eliminated or combined depending on the material employed and the properties thereof. For example, referring to FIG. 2, the lower protective layer 26 and securing layer 30 may be combined into a single layer, which is shown in FIG. 4. More specifically and referring to FIG. 4, a pill 52 is shown having a convex surface, although a planar or concave surface may be employed without limiting the scope of the present invention. A marker assembly 54 is secured to the pill 52. In the current example, the marker assembly 54 includes a lower layer 56, an upper layer 58, and a device 60, such as an IEM. According to one aspect of the present invention, the lower layer 56 is a material that combines both the adhesive and protective properties of layer 30 and layer 26 of FIG. 2, respectively. In a similar manner, upper layer 58 is a material that combines the protective and decorative properties of layer 28 and layer 32 of FIG. 2, respectively. Also, in the current example, the marker assembly 54 is a different size relative to the pill 52. The scope of the present invention is not limited by the shape or size of the marker assembly 54 in this example or any other example disclosed herein.

Referring now to FIG. 5, a pill 62 is shown having a convex surface, although a planar or concave surface may be employed without limiting the scope of the present invention. A marker assembly 64 is secured to the pill 62. In the current example, the marker assembly 64 includes an upper layer 66 and a device 68, such as an IEM. In the current example, the adhesive layer and its properties, such as the adhesive layer 30 of FIG. 2, may be part of the coating on the pill 62. Alternatively, according to another aspect of the present invention, the adhesive layer may be part of the device 68. In yet another aspect of the present invention the adhesive properties may be provided by the upper layer 66 at the contact points with the pill 62. Thus, depending on the properties of the materials selected, the properties of each layer can be altered to the specific needs of that aspect as shown in the various examples.

Figure 5B:
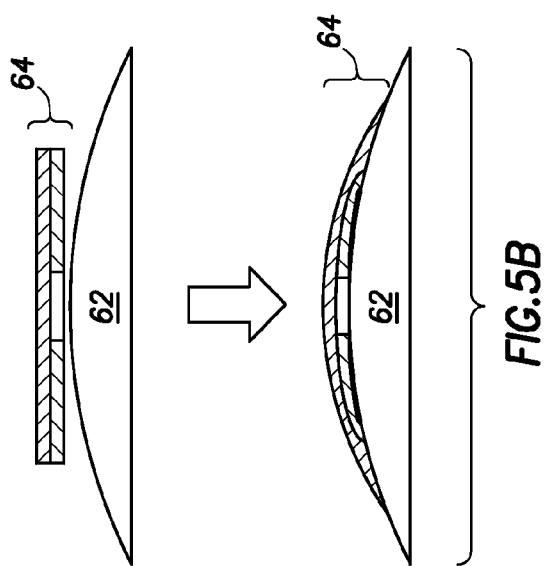
FIG. 5B shows the assembling process of the tablet of FIG. 5.
Figure 5A:
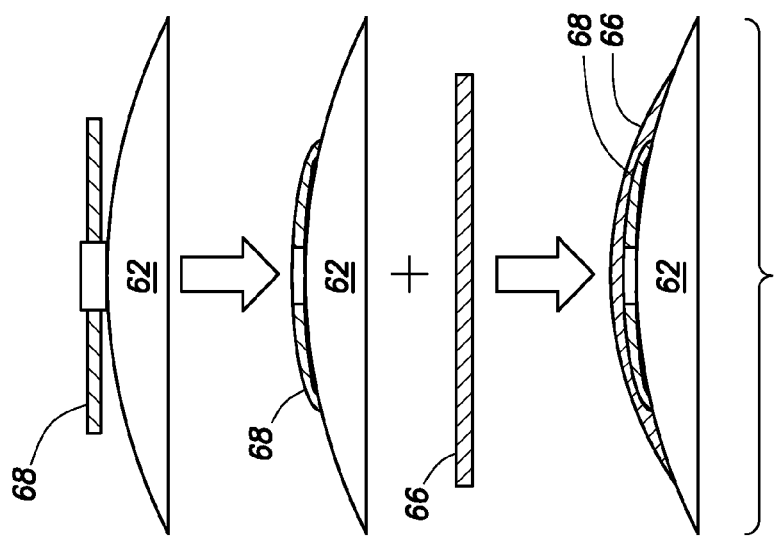
FIG. 5A shows the assembling process of the tablet of FIG. 5.

Referring now to FIG. 5A, the process of assembling the marker assembly 64 onto the pill 62 is shown in accordance with one aspect of the present invention. The marker assembly 64 is built one layer at a time onto the pill 62. The device 68 is positioned on the pill 62. The device 68 is then formed to the shape of the pill 62. The device 68 can be shaped to the shape of the pill 62 using any standard method, e.g., heat and/or pressure. Then the upper layer 66 is added and shaped to the shape of the pill 62 as well as secured thereto using pressure and/or heat.

Referring now to FIG. 5B, the process of assembling the marker assembly 64 onto the pill 62 is shown in accordance with another aspect of the present invention. In this example, the marker assembly 64 is assembled prior to being presented to the pill 62. The marker assembly 64 is positioned on the pill 62. Then the marker assembly 64 is secured to and formed to the shape of the pill 62 using heat and/or pressure.

Figure 6A:
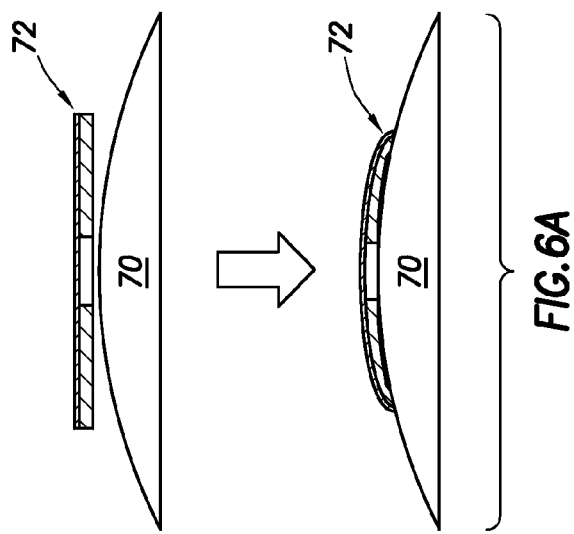
FIG. 6A shows the assembling process of the tablet of FIG. 6.
Figure 6:
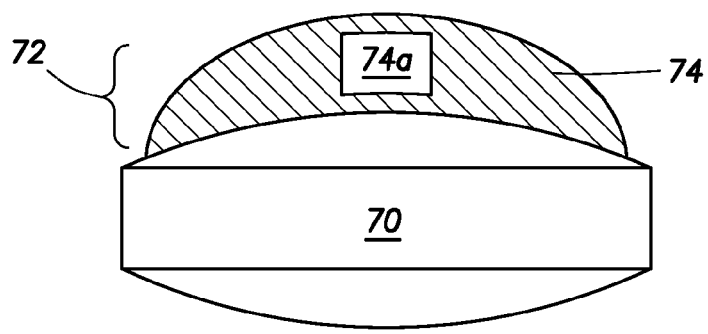
FIG. 6 shows a tablet with a device assembly secured on one surface in accordance with one aspect of the present invention.

Referring now to FIG. 6 and FIG. 6A, in yet another example according to another aspect of the present invention, a pill 70 includes a convex surface, although a planar or concave surface may be employed without limiting the scope of the present invention. A marker assembly 72 is formed to the shape of and secured to the pill 70 using heat and/or pressure. In the current example, the marker assembly 72 includes a device coating layer 74 and a device 74a, such as an IEM. In the current example, the adhesive layer and its properties and the protective layer and its properties, such as the adhesive layer 30 and protective layers 26 and 28 of FIG. 2, are part of the device coating layer 74. Additionally, the properties of the decorative layer 32 of FIG. 2 may also be part of the device coating layer 74.

Figure 7:
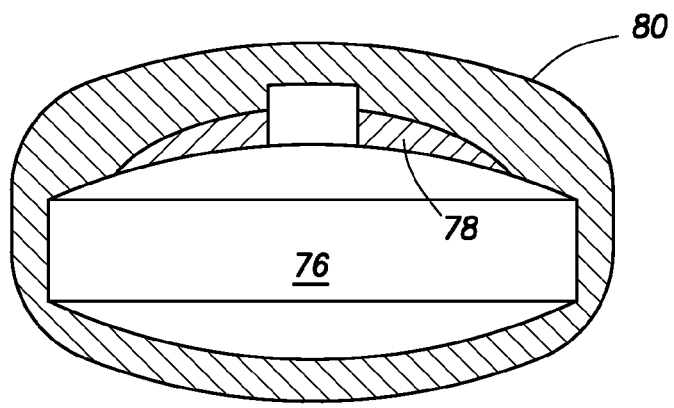
FIG. 7 shows a tablet with a device assembly secured on one surface and a coating that surrounds the tablet in accordance with one aspect of the present invention.

Referring now to FIG. 7, in yet another example according to another aspect of the present invention, a pill 76 includes a convex surface, although a planar or concave surface may be employed without limiting the scope of the present invention. A marker 78 is secured to the pill 76. An enclosing layer 80 surrounds the pill 76 and the marker 78. In the current example, the properties of the adhesive layer, the protective layers, and the decorative layer (such as the layer 30 and layers 26/28 and layer 32 of FIG. 2, respectively) may be part of the enclosing layer 80. In an alternative aspect of the present invention, the marker 78 may have the adhesive properties instead of or in addition to the enclosing layer 80.

Figure 8:
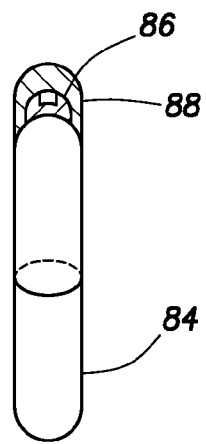
FIG. 8 shows a capsule with a device assembly secured on one end in accordance with one aspect of the present invention.

Referring now to FIG. 8, in yet another example according to another aspect of the present invention, a capsule 84 is shown. A marker 86 is secured to one end of the capsule 84. A layer 88 surrounds the marker 86 and is also secured to the capsule. In the current example, the properties of the adhesive layer, the protective layers, and the decorative layer (such as the layer 30 and layers 26/28 and layer 32 of FIG. 2, respectively) may be incorporated into the layer 88. In an alternative aspect of the present invention, the marker 86 may have the adhesive properties instead of or in addition to the layer 88.

Figure 9:
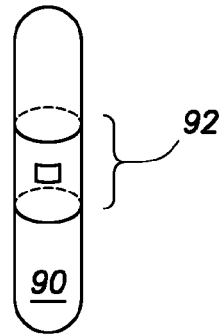
FIG. 9 shows a capsule with a device assembly secured on the side surface in accordance with one aspect of the present invention.

Referring now to FIG. 9, in yet another example according to another aspect of the present invention, a capsule 90 is shown. A marker assembly 92 is secured to mid-portion the capsule 90. The marker assembly 92 surrounds the circumference of the capsule 90. However, the marker assembly 92 may be designed to only partially surround the capsule 90 (not shown), in accordance with another aspect of the present invention. In the current example, the properties of the adhesive layer, the protective layers, and the decorative layer (such as the layer 30 and layers 26/28 and layer 32 of FIG. 2, respectively) may be incorporated into the marker assembly 92.

Figure 10:
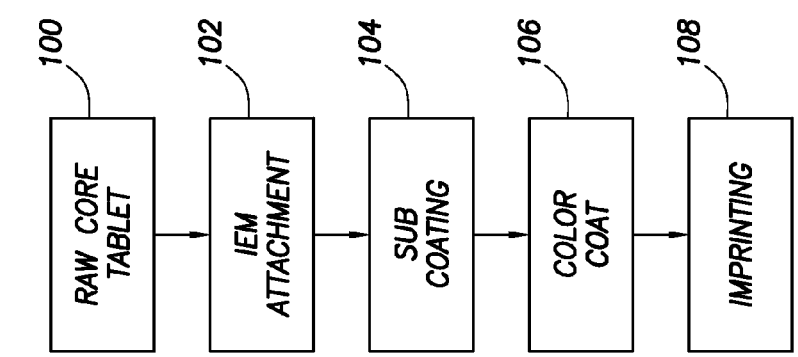
FIG. 10 is a flow process for assembling a device on a tablet in accordance with one aspect of the present invention.

Referring now to FIG. 10, the process steps of securing a device or a device assembly onto a tablet or pill is shown beginning with the step 100 wherein a raw core tablet or pill is created. At step 102, the device or the device assembly is attached to the raw core tablet to create an assembled tablet. At step 104, a sub coating is added to the assembled tablet to create a coated tablet. At step 106, which is an optional step, color coating is added to the coated tablet to create a color coated tablet. At step 108, which is an optional step, the color coated tablet is imprinted to produce an imprinted tablet that is ready for distribution.

Figure 11:
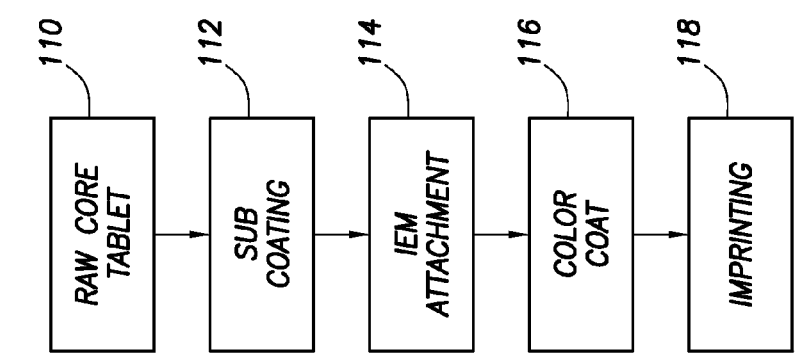
FIG. 11 is a flow process for assembling a device on a tablet in accordance with one aspect of the present invention.

Referring now to FIG. 11, the process steps of securing a device or a device assembly onto a tablet or pill in accordance with another aspect of the present invention is shown beginning with the step 110 wherein a raw core tablet or pill is created. At step 112, a sub coating is added to the raw core tablet to create a coated tablet. At step 114, the device or the device assembly is attached to the coated tablet to create an assembled coated tablet. At step 116, which is an optional step, color coating is added to the assembled coated tablet to create a color coated tablet. At step 118, which is an optional step, the color coated tablet is imprinted to produce an imprinted tablet that is ready for distribution.

Figure 12:
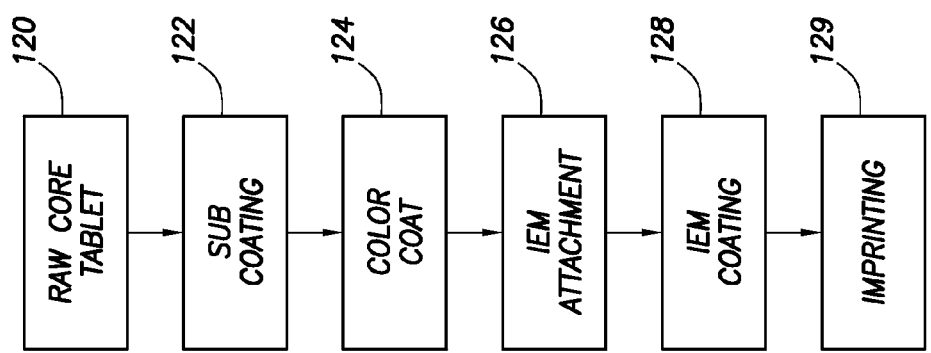
FIG. 12 is a flow process for assembling a device on a tablet in accordance with one aspect of the present invention.

Referring now to FIG. 12, the process steps of securing a device or a device assembly onto a tablet or pill in accordance with yet another aspect of the present invention is shown beginning with the step 120 wherein a raw core tablet or pill is created. At step 122, a sub coating is added to the raw core tablet to create a coated tablet. At step 124, color coating is added to the coated tablet to create a color coated tablet. At step 126, a device or the device assembly is attached to the color coated tablet to create an assembled color coated tablet. At step 128, a second coating is added to the assembled color coated tablet to create an enclosed assembled tablet. At step 129, which is an optional step, the enclosed assembled tablet is imprinted to produce an imprinted tablet that is ready for distribution.

Figure 14:
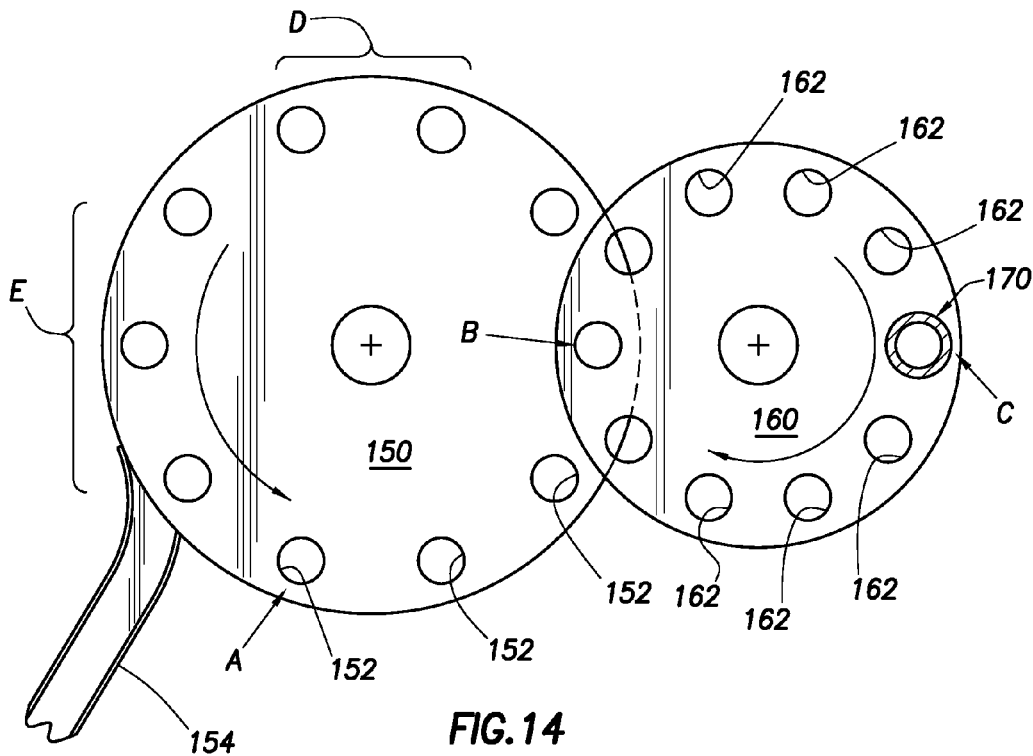
FIG. 14 is an assembling apparatus for assembling a device on a tablet.
Figure 15:
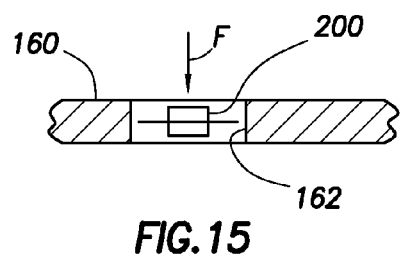
FIG. 15 is a close-up view of a portion of a portion of the apparatus of FIG. 14 with specific indication of the direction of force applied.
Figure 16:
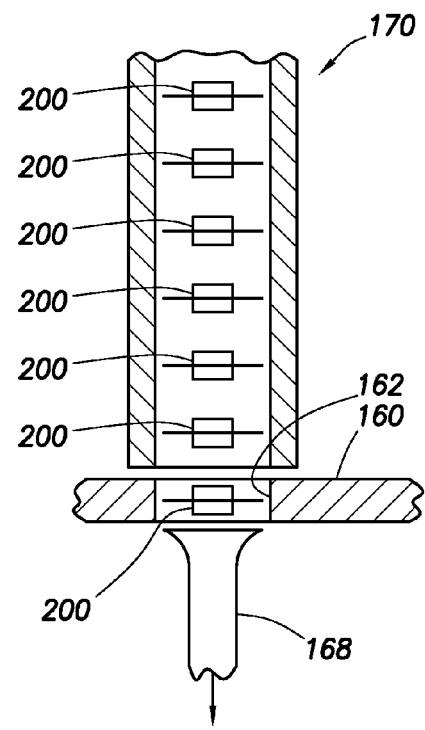
FIG. 16 is a close-up view of a portion of a feeder assembly of the apparatus of FIG. 14.

Referring now to FIG. 14, FIG. 15, and FIG. 16, a tablet press 150 is shown. The press 150 rotates in a counter-clockwise direction as shown. The press 150 includes die cavity or punch cavity 152 and an ejection tray 154. Starting at position A, as shown, the pharmaceutical product is deposited in the cavity 152. The press 150 rotates to position B, which is positioned below a transfer wheel 160. The wheel 160 includes several openings 162. As the wheel 160 passes position C, each opening 162 passes under a feeder 170, as shown in FIG. 16.

The feeder 170 contains marker devices 200. The device 200 is an IEM that is activated upon contact with a conducting fluid. The scope of the present invention is not limited by the environment or type of the conducting fluid. Once ingested, the device 200 comes into contact with a conducting fluid, such as stomach fluids, and the device 200 is activated. Referring again to the instance where the device 200 is used with the product that is ingested by the living organism, when the product that includes the device 200 is taken or ingested, the device 200 comes into contact with the conducting liquid of the body and a voltage potential is created and the system is activated. A portion of the power source is provided by the device 200, while another portion of the power source is provided by the conducting fluid.

Referring again to FIG. 14 and FIG. 15, each time an opening 162 passes under the feeder 170, one of the devices 200 is dropped into the opening 162 directly under the feeder 170. As shown in FIG. 15, a force "F" is shown to assist the movement of the device 200 from the feeder 170 into the opening 162. The force may be provided by the use of a vacuum through a suction tube 168. In accordance with other aspects of the present invention, the force may be provided by a spring, an air burst, or an ejection pin in addition to gravity. The wheel 160 rotates to position B. At position B, the device 200 located in the opening 162 is dropped into the cavity 152 of the press 150. The press 150 rotates to the position D where additional pharmaceutical product is deposited into the cavity 152 on top of the device 200. The press 150 continues to move in the counter-clockwise direction and at position E, the content of the cavity 152 is pressed under high pressure to form a tablet with the device 200 inside. The completed tablet is ejected and moved to a collection point through the ejection tray 154 for further processing, such as coating layers as needed.

Figure 17:
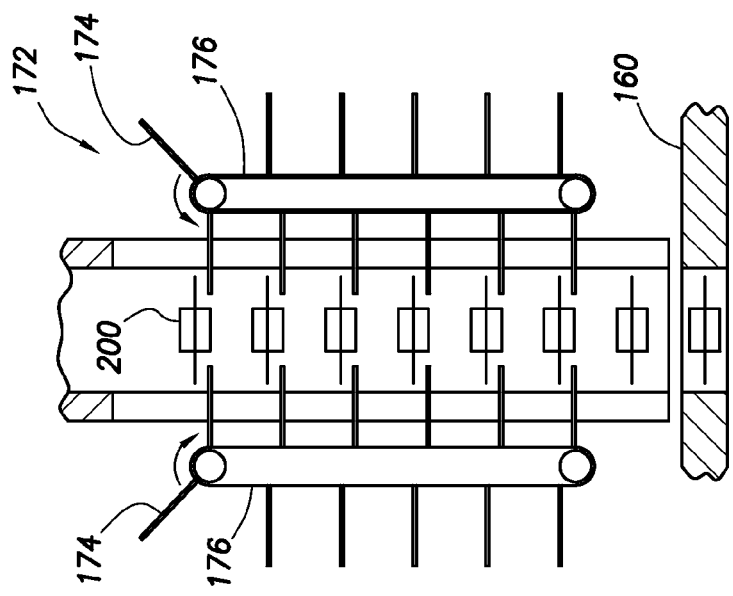
FIG. 17 is a close-up view of a portion of a feeder assembly that can be used with the apparatus of FIG. 14 in accordance with another aspect of the present invention.

Referring now to FIG. 17, a feeder assembly 172 is shown as alternative embodiment and in accordance with another aspect of the present invention. The feeder assembly 172 can be used in place of the feeder 170 of the FIG. 14. The feeder assembly 172 includes a plurality of supporting fingers 174 that hold each device 200 in position. The fingers 174 are connected to a belt 176. The fingers 174 lower the device 200 toward the wheel 160 of FIG. 14. When the fingers 174 reach the lower portion near the wheel 160, the fingers 174 move apart and drop the device 200 into the opening 162 of the wheel 160.

Figure 18B:
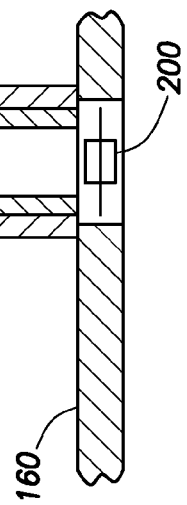
FIG. 18B is a close-up view of a portion of the feeder assembly shown in FIG. 18A at an advanced stage in the loading process.
Figure 18A:
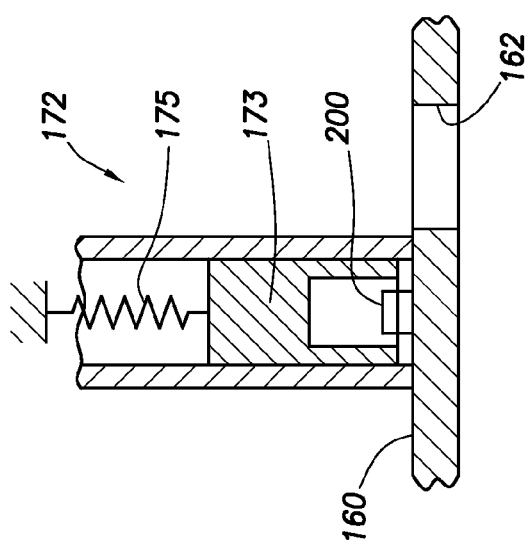
FIG. 18A is a close-up view of a portion of a feeder assembly that can be used with the apparatus of FIG. 14 in accordance with another aspect of the present invention.

Referring now to FIG. 18A and FIG. 18B, in accordance with another aspect of the present invention, the feeder assembly 172 includes an ejector 173 with a spring 175. As the opening 162 moves under the feeder assembly 172, the ejector 173 pushes the device 200 into the opening 162 of the wheel 160.

Figure 24A:
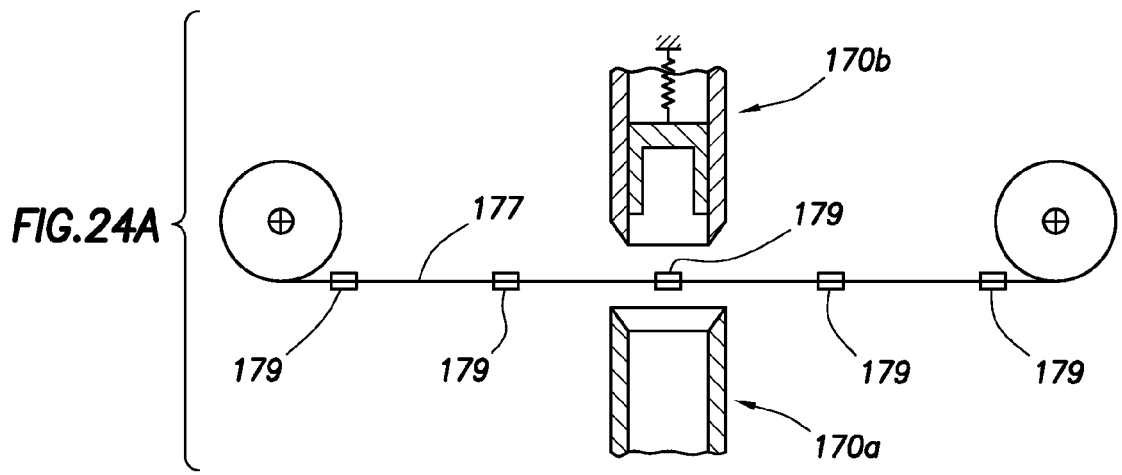
FIGS. 24A-C show a process for loading a feeder or a feeder assembly of any of FIG. 16, FIG. 17, FIG. 18A, and FIG. 18B.
Figure 24B:
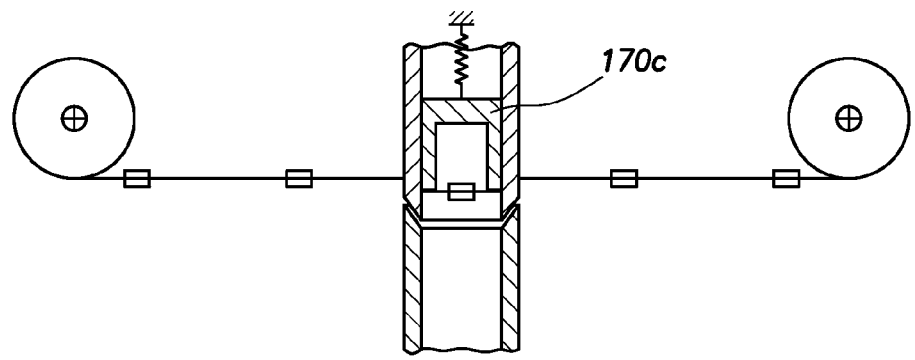
Figure 24C:
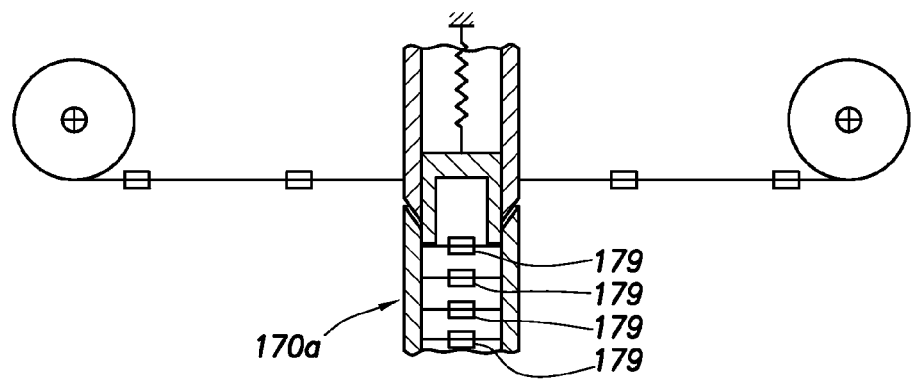

Referring now to FIG. 24A, FIG. 24B, and FIG. 24C, an alternative example of a feeder assembly 170a is shown positioned below a cutting tool 170b. A web sheet 177 is positioned between the feeder assembly 170a and the tool 170b. The web sheet 177 delivers devices 179 to a position above the feeder assembly 170a. As shown in FIG. 24B, the tool 170b moves toward the feeder assembly 170a and cuts out the device 179. An ejector 170c moves downward to push the device 179 out of the tool 170b and into the feeder assembly 170a. As shown in FIG. 24C, the process continues and the devices 179 are fed into the feeder assembly 170a. This process can be used to load the feeder 170 of FIG. 16. In accordance with another aspect of the present invention, the feeder assembly 170a can be used to replace the feeder 170 of FIG. 14 and FIG. 16.

Figure 13:
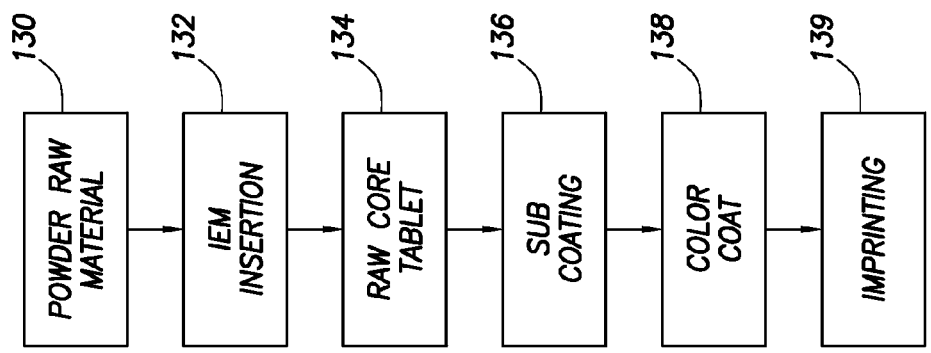
FIG. 13 is a flow process for assembling a device in a tablet in accordance with one aspect of the present invention.

Referring now to FIG. 13, the process steps of assembling a device 200 within the tablet or pill is shown beginning with the step 130 wherein the powder/raw material is loaded into the mold. At step 132 the device 200 is inserted into the mold. At step 134 more powder/raw material is added and a raw core tablet or pill is created. At step 134 a coating layer is added to the raw core tablet to create a coated tablet. At step 138, color coating is added to the coated tablet to create a color coated tablet. At step 139, which is an optional step, the color coated tablet is imprinted to produce an imprinted tablet that is ready for distribution.

Figure 19:
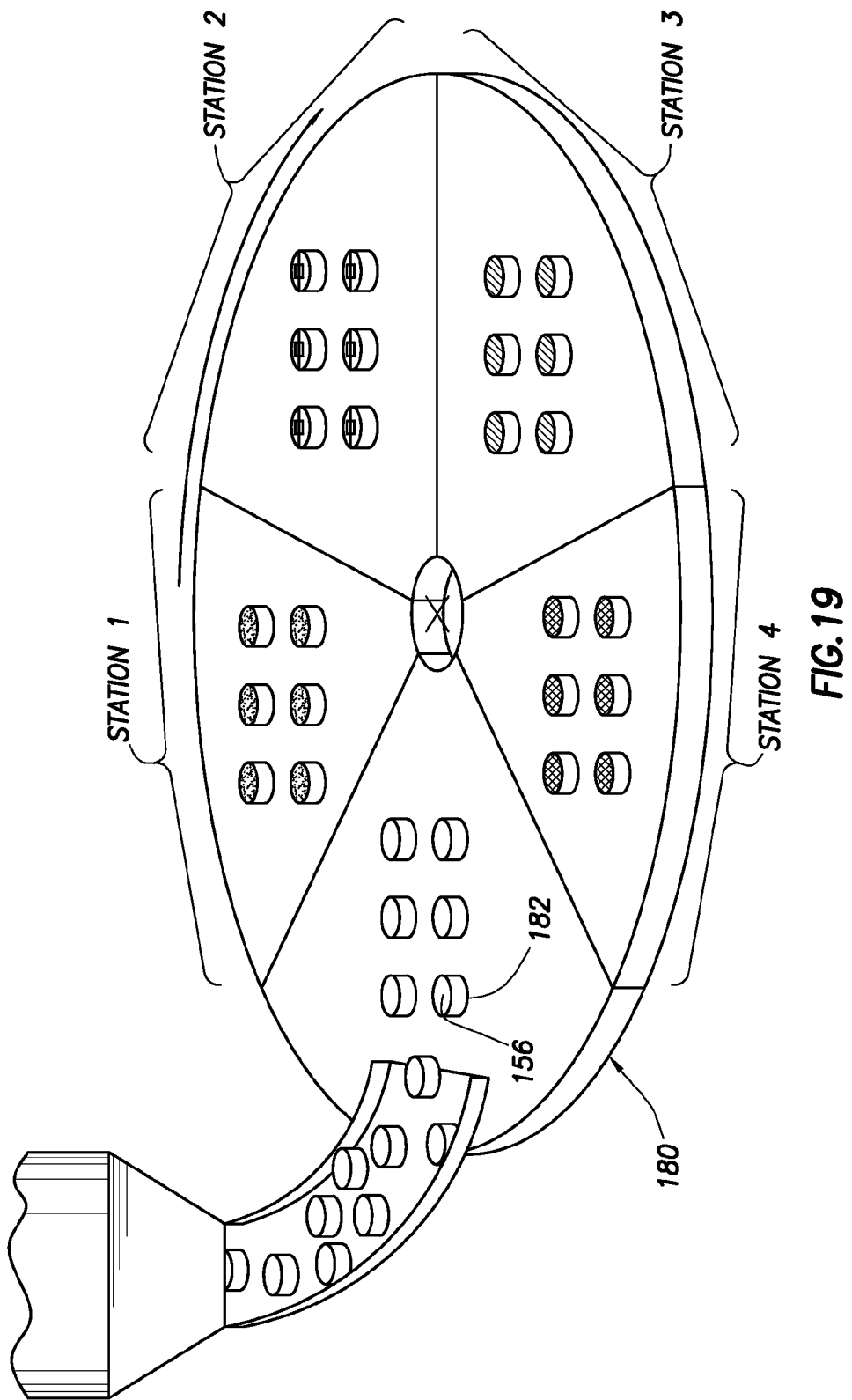
FIG. 19 is an assembly apparatus for the assembly of a device on a tablet in accordance with one aspect of the present invention.
Figure 20:
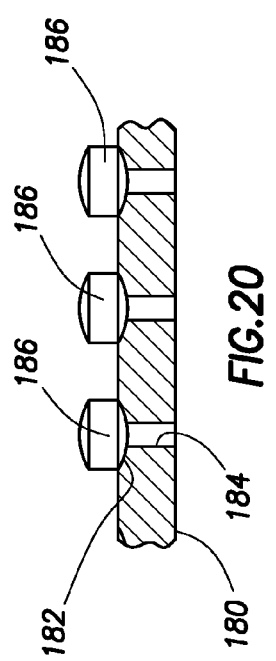
FIG. 20 is a close-up view of a portion of the assembly apparatus of FIG. 19.

In accordance with another aspect of the present invention, the device 200 may be secured to the exterior of the product. The process of assembling or securing the device 200 to the exterior of the product can be done using an assembly array. Referring now to FIG. 19 and FIG. 20, a wheel 180 is shown that includes positional grooves 182. The grooves 182 are shown in greater detail in FIG. 20. Each groove 182 has an opening 184 therein. A vacuum is created through the opening 184 that draws pills 186 into position as the pills 186 are delivered to the wheel 180 from a hopper tray 188. In accordance with other aspects of the present invention, the pills 186 can be positioned by other methods than vacuum draw. The pills 186 can be vibrated into position or brushed over with some form of sweeper so they fall into the hole and excess are brushed off. As the wheel 180 rotates the pill 186 moves to station 1 where an adhesive layer is applied. As the wheel 180 moves to station 2, the device 200 is secured to each pill 186. As the wheel 180 moves to station 3 a protective layer is applied. As the wheel 180 moves to station 4, a decorative or printed layer is applied. Thereafter, the complete and printed tablets or pills 186 are removed from the wheel 180 to a central collection point for further processing or distribution. The scope of the present invention is not limited by the number of stations on the wheel 180. For example, there wheel 180 can be designed to have one station, at which station a pre-assembled device is applied to the pill 186. The pre-assembled device can be as simple as the IEM with an adhesive layer or as discussed above with respect to FIG. 1.

Figure 21:
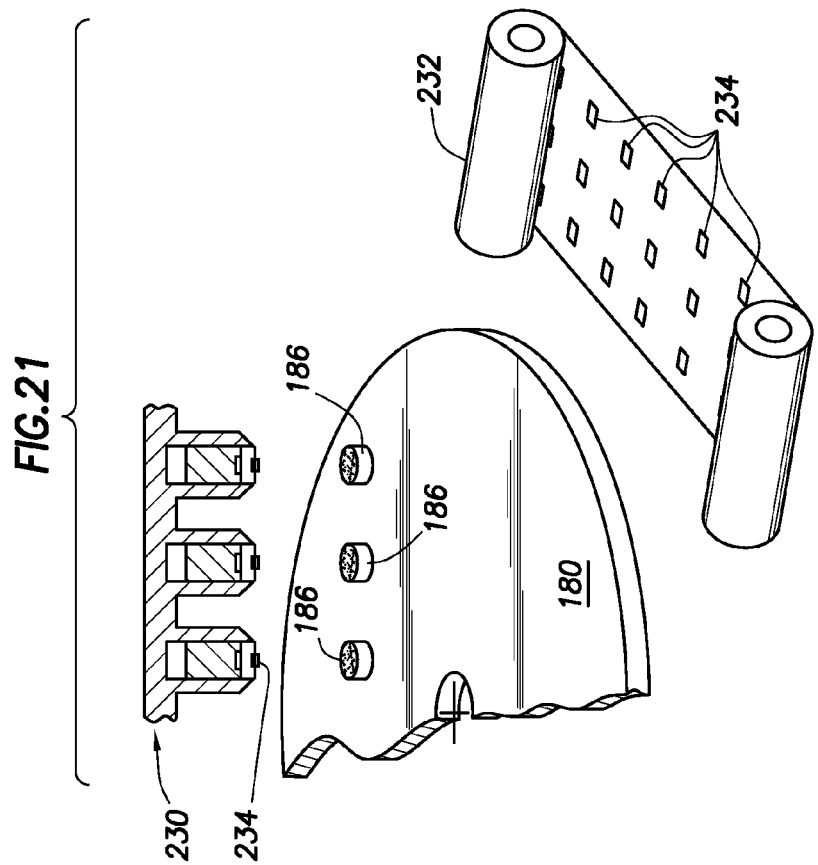
FIG. 21 is a view of the assembly apparatus that includes additional components used in assembling the device onto a tablet or pill as shown partially in FIG. 19.

Referring now to FIG. 21, at each station shown in FIG. 19 various assembly steps are carried out including installation of the device on the tablet as well as other components or parts. A portion of a delivery arm 230 is shown positioned over a portion of the pills 186. The delivery arm 230 moves between the wheel 180 and a web 232. The web 232 contains devices 234 arranged in order to allow for the delivery arm 230 to pick up the devices 234. The delivery arm 230 removes the devices 234 from the web 232 and secures the devices 234 to the pills 186. In accordance with another aspect of the present invention the devices 234 are cut or punched out of the web 232. At other stations, other delivery arms remove or punch out or cut out other materials from different web rolls and secure those materials to the pills 186. For example, the delivery arm can remove a protection layer from the web sheet and secure it to a tablet with a device already secured thereto. According to another aspect of the present invention, the devices positioned on the web may be a marker assembly unit such that a single installation process is all that is needed and each station can be used to perform the single task of moving the marker assembly from the web to the pill 186 using the delivery arm 230.

Figure 22:
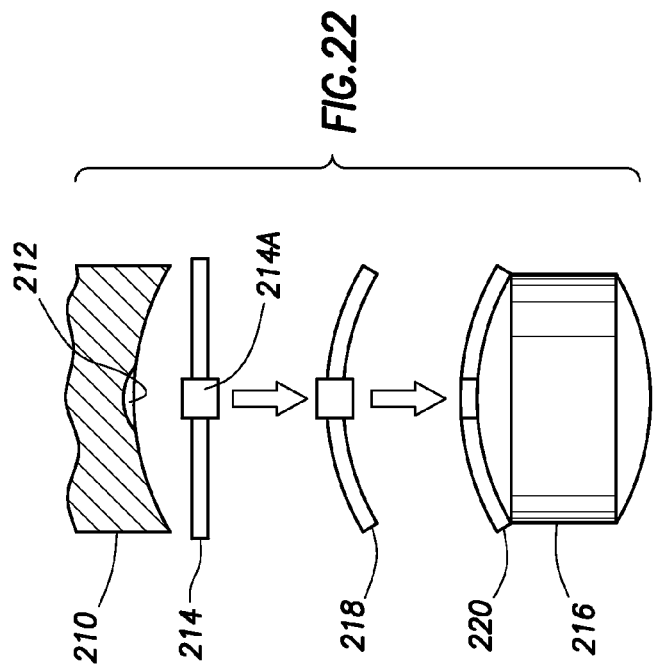
FIG. 22 is a close-up view of a pressing tool in accordance with one aspect of the present invention.

Referring now to FIG. 22, an assembly process is shown wherein a tool 210 includes a cavity 212. The tool 210 is positioned above an assembly device 214, which includes circuitry 214*a*, prior to formation of the device onto a pill or tablet 216. The tool 210 is formed to the shape of the tablet 216 and is lowered onto the device 214. Through the application of temperature and pressure the device 214 is reformed as device 218 and secured to the tablet 216 as device 220. The cavity 212 prevents pressure from being applied to the circuitry 214*a* of the device 214.

Figure 23A:
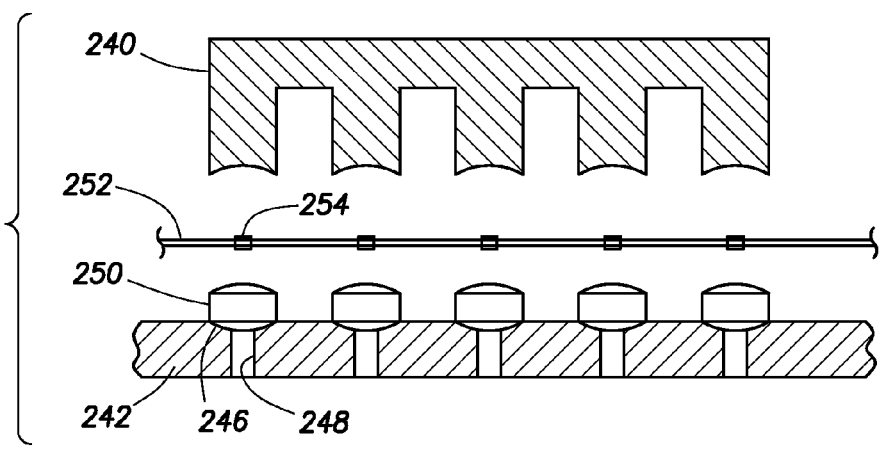
FIGS. 23A-C show an assembly apparatus for assembling a device onto a tablet according to another aspect of the present invention.
Figure 23B:
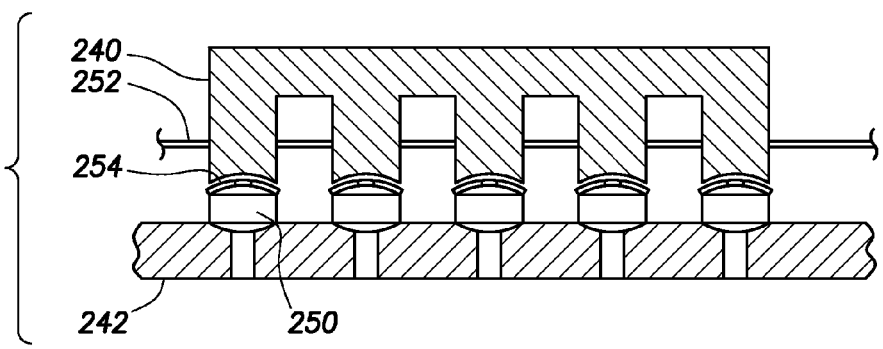
Figure 23C:
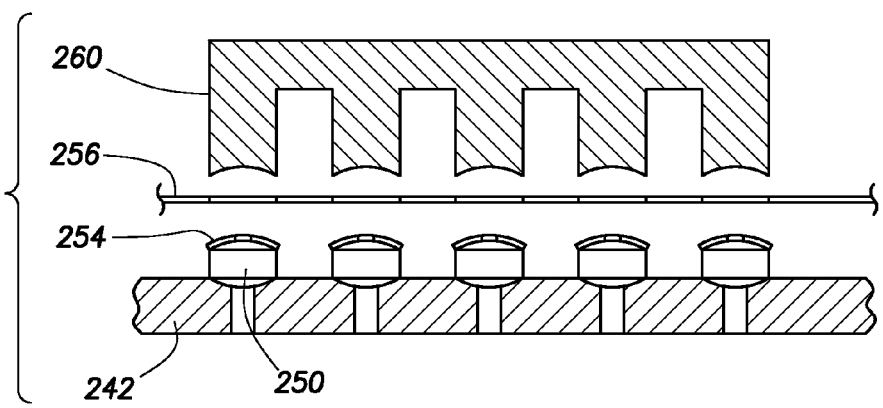

Referring now to FIG. 23A, FIG. 23B, and FIG. 23C, according to another aspect of the present invention, an alternative assembly process is shown wherein a pressing tool or cutting tool 240 is positioned above a press table 242. The table 242 includes grooves 246 that have a central hole 248. The tablet 250 is held in the groove 246 using a vacuum suction applied through the hole 248. A web sheet 252 is positioned between the table 242 and the tool 240. The sheet 252 includes devices 254. To begin the assembly process, the tool 240 moves toward the table 242. The sheet 252 is punched and the device 254 is secured to the tablet 250 as shown in FIG. 23B. At a different station or position in the assembly process, a sheet 256 that includes a different layer in the assembly process is positioned between the table 242 that now holds the tablet 250 with the device 254 secured thereto and a cutting tool 260. The cutting tool 260 moves toward the table 242 and secures the layer 256 onto the tablet 250 (not shown) to form a coated tablet 250 with a device 254 assembled thereto.

Figure 25:
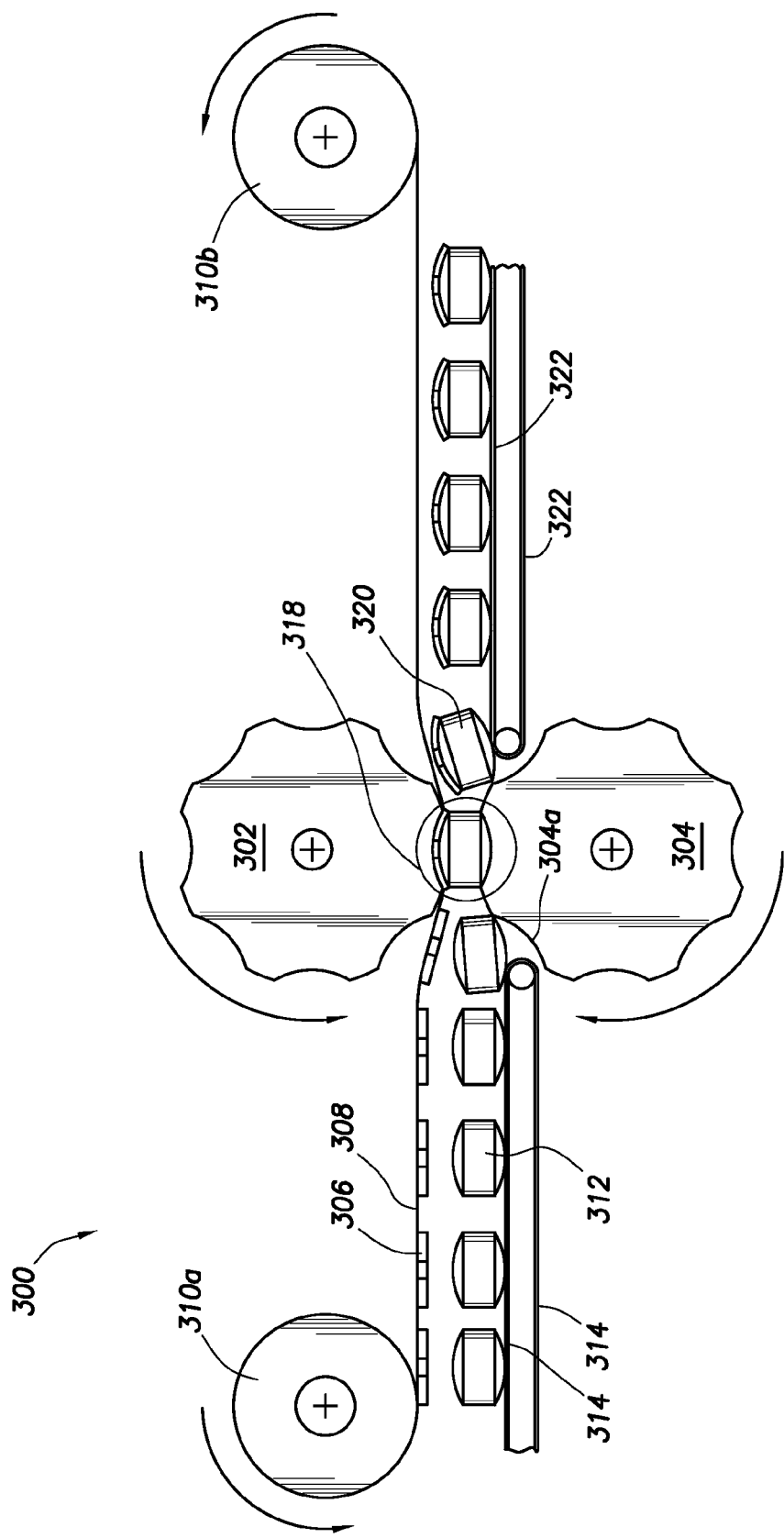
FIG. 25 shows an assembly apparatus using a process for assembling a device onto a tablet or pill in accordance with another aspect of the present invention.

Referring now to FIG. 25, an assembly process is shown in accordance with another aspect of the present invention. An assembly unit 300 includes a press 302 and a press 304. The press 302 is positioned above a web 308. The web 308 has devices 306 positioned and held in place on the web 308. Devices 306 have an adhesive layer holding them to the web 308 and a second adhesive layer positioned on the opposite side adjacent to the tablets 312. As the web 308 moves from a roller 310*a* to a roller 310*b*, the devices are presented and positioned above tablets 312, which are positioned on a tablet feeder belt 314. The feeder belt 314 moves the tablets 312 towards the press 304 as the devices 306 move toward the press 302. As the tablets 312 approach the press 304, each tablet 312 falls into a groove 304*a* of the press 304. The tablet 312 is then lifted by the press 304 toward the press 302 as the press 302 pushes the device 306 toward the press 304. At position 318 the device 306 is pressed onto the tablet 312 and secured thereto. As the press 302 and press 304 rotate the web 308 moves toward the roller 310*b*. At the same time, an assembled tablet 320 is lowered onto a take away roller belt 322 that moves the assembled tablet 320 away from the press 302 and the press 304. The assembled tablets 320 may be moved to the next phase of the process including packaging for distribution or additional preparation steps such as adding additional layers or coatings.

Embodiments of interest include high-throughput fabrication processes, e.g., where details regarding such embodiments are provided above and/or in U.S. Provisional Application Ser. No. 61/142,849; the disclosure of which is herein incorporated by reference.

As described herein, a system of the present invention is used with a conducting fluid to indicate the event marked by contact between the conducting fluid and the system. For example, the system of the present disclosure may be used with a pharmaceutical product and the event that is indicated is when the product is taken or ingested. The term "ingested" or "ingest" or "ingesting" is understood to mean any introduction of the system internal to the in-vivo. For example, ingesting includes simply placing the system in the mouth all the way to the descending colon. Thus, the term ingesting refers to any instant in time when the system is introduced to an environment that contains a conducting fluid. Another example would be a situation when a non-conducting fluid is mixed with a conducting fluid. In such a situation the system would be present in the non-conduction fluid and when the two fluids are mixed, the system comes into contact with the conducting fluid and the system is activated. Yet another example would be the situation when the presence of certain conducting fluids needed to be detected. In such instances, the presence of the system, which would be activated, within the conducting fluid could be detected and, hence, the presence of the respective fluid would be detected.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A pharmaceutical product comprising:
    a pill; and
    a device including a top and a bottom, and secured to the pill, wherein the device comprises:
        a non-conductive skirt that defines a central cavity;
        a control unit positioned in the central cavity defined by the skirt, wherein the control unit includes at least a first material and a second material, wherein the first material is dissimilar from the second material, and wherein the first and second materials are positioned on opposite sides of the control unit and electrically connected thereto, wherein the first material is exposable at a first side of the skirt and the second material is exposable at a second side of the skirt such that the skirt separates the two dissimilar materials when exposed, wherein, when the first and second materials are exposed and in contact with a conductive fluid a voltage potential for powering the control unit is generated and a current flow is produced through the conductive fluid between the first and second materials that extends around the non-conductive skirt, and wherein the control unit, when powered, modulates the current flow to generate a current signature with information encoded in the current signature; and
        a securing portion on the bottom of the device for securing the device to the pill.

2. The product of claim 1, further comprising a protective layer positioned on top of the device.

3. The product of claim 2, wherein the protective layer is the same size as the skirt and covers the top of the control unit.

4. The product of claim 2, wherein the securing portion is a plurality of adhesive dots positioned on the bottom of the device on the skirt.

5. The product of claim 4, wherein the securing portion is the same size as the device and covers the bottom of the device.

6. The product of claim 2, further comprising a second protective layer positioned on the bottom of the device and between the device and the securing portion.

7. The product of claim 6, wherein the second protective layer is the same size as the skirt and covers the bottom of control unit.

8. The product of claim 6, wherein the securing portion is a plurality of adhesive dots positioned on the second protective layer and about the device.

9. The product of claim 6, wherein the securing portion is the same size as the device and positioned onto the second protective layer.

10. A pharmaceutical product with an ingestible electronic marker, the product comprising:
    a first tablet portion containing a drug; and
    a second tablet portion containing a fast dissolving agent, wherein the agent and drug are chemically compatible,
    wherein the first tablet portion and second tablet portion define a cavity for holding the ingestible electronic marker, and
    wherein the ingestible electronic marker includes:
    a non-conductive skirt that defines a central cavity;
    a control unit positioned in the central cavity defined by the skirt,
    wherein the control unit includes at least two dissimilar materials separated by the skirt,
    wherein the two dissimilar materials form a partial power source completable upon contact with a conductive fluid to provide a voltage potential to power the control unit, and wherein, when powered, the control unit generates a current signature with information encoded in the current signature; and
    a coating to define a pocket that surrounds the skirt and control unit, wherein the coating dissolves away to expose the control unit to the surrounding environment.

11. The product of claim 10, wherein the tablet is placed inside of a capsule.

12. The product of claim 10, wherein the capsule is filled with a second drug.

* * * * *

UNITED STATES PATENT AND TRADEMARK OFFICE
CERTIFICATE OF CORRECTION

| | | |
|---|---|---|
| PATENT NO. | : 8,784,308 B2 | Page 1 of 1 |
| APPLICATION NO. | : 13/319309 | |
| DATED | : July 22, 2014 | |
| INVENTOR(S) | : Hafezi et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 97 days.

Signed and Sealed this
Eighth Day of September, 2015

Michelle K. Lee
*Director of the United States Patent and Trademark Office*